(12) United States Patent
Leonhardt et al.

(10) Patent No.: US 11,691,007 B2
(45) Date of Patent: Jul. 4, 2023

(54) BIOELECTRIC OPG TREATMENT OF CANCER

(71) Applicant: Leonhardt Ventures LLC, Mission Viejo, CA (US)

(72) Inventors: Howard J. Leonhardt, Mission Viejo, CA (US); Jorge Genovese, Buenos Aires (AR)

(73) Assignee: Leonhardt Ventures LLC, Mission Viejo, CA (US)

( * ) Notice: Subject to any disclaimer, the term of this patent is extended or adjusted under 35 U.S.C. 154(b) by 102 days.

(21) Appl. No.: 16/913,964

(22) Filed: Jun. 26, 2020

(65) Prior Publication Data
US 2020/0330759 A1   Oct. 22, 2020

Related U.S. Application Data

(63) Continuation-in-part of application No. 16/137,035, filed on Sep. 20, 2018, now Pat. No. 11,185,691, and a continuation-in-part of application No. 15/812,760, filed on Nov. 14, 2017, now Pat. No. 10,960,206, and a continuation-in-part of application No. 15/471,954, filed on Mar. 28, 2017, now Pat. No. 10,695,563, said application No. 15/812,760 is a continuation-in-part of application No. 15/460,129, filed on Mar. 15, 2017, said application No. 16/137,035 is a continuation-in-
(Continued)

(51) Int. Cl.
*A61N 1/36* (2006.01)
*A61N 1/375* (2006.01)
*A61K 45/06* (2006.01)

(52) U.S. Cl.
CPC ......... *A61N 1/36002* (2017.08); *A61N 1/375* (2013.01); *A61K 45/06* (2013.01)

(58) Field of Classification Search
CPC .... A61N 1/36002; A61N 1/375; A61K 45/06; A61M 5/14244
See application file for complete search history.

(56) References Cited

U.S. PATENT DOCUMENTS

D263,073 S   2/1982   Jonkers et al.
D273,893 S   5/1984   Weitzman
(Continued)

FOREIGN PATENT DOCUMENTS

AU   2019363173 A3   4/2020
CA      2685161 A1   10/2007
(Continued)

OTHER PUBLICATIONS

Leonhardt's Launchpads Announces Filing og Patent for Bioelectric Stimulation Controlled Klotho Expression—Powerful Anti-aging and Regeneration Promoting Protein, by API Podder, Published Mar. 13, 2019, available online at: <https://leonhardtventures.com/leonhardts-launchpads-announces-filing-of-patent-for-bioelectric-stimulation-controlled-klotho-expression-powerful-anti-aging-and-regeneration-promoting-protein/> Mar. 13, 2019.*

(Continued)

*Primary Examiner* — Mark W. Bockelman
(74) *Attorney, Agent, or Firm* — TraskBritt

(57) ABSTRACT

Described is a method of treating a subject diagnosed with cancer, breast cancer, bone cancer, lung cancer, osteoporosis, multiple myeloma, and a combination of any thereof by applying a bioelectric signal or signals that upregulate the expression of Osteoprotegerin ("OPG") and thus beneficially effect the subject's OPG/RANKL/RANK pathway.

12 Claims, 6 Drawing Sheets

Related U.S. Application Data part of application No. 15/460,129, filed on Mar. 15, 2017.

(60) Provisional application No. 62/454,521, filed on Feb. 3, 2017, provisional application No. 62/385,124, filed on Sep. 8, 2016, provisional application No. 62/375,271, filed on Aug. 15, 2016, provisional application No. 62/364,472, filed on Jul. 20, 2016, provisional application No. 62/363,012, filed on Jul. 15, 2016, provisional application No. 62/352,930, filed on Jun. 21, 2016, provisional application No. 62/314,240, filed on Mar. 28, 2016, provisional application No. 62/308,702, filed on Mar. 15, 2016.

(56) References Cited

U.S. PATENT DOCUMENTS

| | | |
|---|---|---|
| 4,622,952 A | 11/1986 | Gordon |
| 4,976,733 A | 12/1990 | Girardot |
| 5,135,478 A | 8/1992 | Sibalis |
| 5,211,622 A | 5/1993 | Liboff et al. |
| 5,295,958 A | 3/1994 | Shturman |
| 5,543,318 A | 8/1996 | Smith et al. |
| 5,555,883 A * | 9/1996 | Avitall ................. A61B 5/6856 600/374 |
| 5,693,029 A | 12/1997 | Leonhardt |
| 5,713,917 A | 2/1998 | Leonhardt et al. |
| 5,725,377 A | 3/1998 | Lemler et al. |
| 5,817,139 A | 10/1998 | Kasano |
| 5,957,949 A | 9/1999 | Leonhardt et al. |
| 6,047,700 A | 4/2000 | Eggers et al. |
| 6,344,052 B1 | 2/2002 | Greenan et al. |
| 6,618,625 B2 | 9/2003 | Silverstone |
| 6,957,106 B2 | 10/2005 | Schuler et al. |
| 6,988,004 B2 | 1/2006 | Kanno et al. |
| 7,029,276 B2 | 4/2006 | Mao |
| 7,136,699 B2 | 11/2006 | Palti |
| 7,341,062 B2 | 3/2008 | Chachques et al. |
| 7,483,749 B2 | 1/2009 | Leonhardt et al. |
| 7,686,799 B2 | 3/2010 | Leonhardt et al. |
| 7,881,784 B2 | 2/2011 | Pasricha et al. |
| 8,041,428 B2 | 10/2011 | Errico et al. |
| 8,133,267 B2 | 3/2012 | Leonhardt et al. |
| 8,166,976 B2 | 5/2012 | Webster et al. |
| 8,226,407 B2 | 7/2012 | Hanewinkel et al. |
| 8,465,533 B2 | 6/2013 | Palti |
| 8,534,289 B2 | 9/2013 | Hernandez |
| 8,639,361 B2 | 1/2014 | Nathanson |
| 8,646,455 B2 | 2/2014 | Webster et al. |
| 8,656,930 B2 | 2/2014 | Schuler et al. |
| 8,660,669 B2 | 2/2014 | Nemeh et al. |
| 8,738,144 B2 | 5/2014 | Schneider |
| 8,909,346 B2 | 12/2014 | Chalmers |
| 8,945,104 B2 | 2/2015 | Boone et al. |
| 9,032,964 B2 | 5/2015 | Schuler et al. |
| 9,173,811 B2 | 11/2015 | Greiner et al. |
| 9,533,170 B2 | 1/2017 | Dye et al. |
| 9,545,331 B2 | 1/2017 | Ingemarsson-Matzen |
| D778,449 S | 2/2017 | Ingemarsson-Matzen |
| 9,656,096 B2 | 5/2017 | Pilla |
| 9,662,184 B2 | 5/2017 | Lowe |
| 9,687,383 B2 | 6/2017 | Ingemarsson-Matzen |
| 9,707,403 B2 | 7/2017 | Schuler |
| 9,855,418 B2 | 1/2018 | Haralambidis |
| 9,987,326 B2 | 6/2018 | Koeffler et al. |
| D832,447 S | 10/2018 | Wiffen |
| 10,543,119 B2 | 1/2020 | Ingemarsson-Matzen |
| 10,561,836 B2 | 2/2020 | Sama |
| D881,399 S | 4/2020 | Ingemarsson-Matzen |
| 10,646,644 B2 | 5/2020 | Leonhardt et al. |
| 10,960,206 B2 | 3/2021 | Leonhardt et al. |
| 11,058,536 B2 | 7/2021 | Huber |
| 11,110,274 B2 | 9/2021 | Leonhardt |
| 2002/0143373 A1 | 10/2002 | Courtnage et al. |
| 2003/0032998 A1 | 2/2003 | Altman |
| 2003/0220556 A1 | 11/2003 | Porat et al. |
| 2004/0010231 A1 | 1/2004 | Leonhardt et al. |
| 2004/0115587 A1 | 6/2004 | Breining et al. |
| 2004/0147906 A1 | 7/2004 | Voyiazis et al. |
| 2004/0236238 A1 | 11/2004 | Schuler et al. |
| 2005/0171578 A1 | 8/2005 | Leonhardt |
| 2006/0030908 A1 | 2/2006 | Powell et al. |
| 2006/0100553 A1 | 5/2006 | Lodin |
| 2006/0116721 A1* | 6/2006 | Yun ................... A61K 31/4168 607/2 |
| 2006/0195164 A1 | 8/2006 | Sondergaard et al. |
| 2007/0123758 A1* | 5/2007 | Miesel ............... A61N 1/36067 607/2 |
| 2007/0167984 A1 | 7/2007 | Kieval et al. |
| 2007/0190028 A1 | 8/2007 | Qu et al. |
| 2007/0265680 A1 | 11/2007 | Liu et al. |
| 2008/0227046 A1 | 9/2008 | Lowe et al. |
| 2008/0243060 A1 | 10/2008 | Hartmann et al. |
| 2009/0132010 A1 | 5/2009 | Kronberg |
| 2009/0240304 A1 | 9/2009 | Blum et al. |
| 2010/0082027 A1 | 4/2010 | Chalmers |
| 2010/0184183 A1 | 7/2010 | Schussler et al. |
| 2012/0156648 A1 | 6/2012 | Kaufman et al. |
| 2013/0253413 A1* | 9/2013 | Levine ................ A61N 1/326 607/51 |
| 2014/0023983 A1 | 1/2014 | Lowe et al. |
| 2014/0214115 A1 | 7/2014 | Greiner et al. |
| 2014/0214116 A1 | 7/2014 | Peterson et al. |
| 2014/0214124 A1 | 7/2014 | Greiner et al. |
| 2014/0214144 A1 | 7/2014 | Peterson et al. |
| 2014/0228910 A1 | 8/2014 | Schuler et al. |
| 2017/0028184 A1 | 2/2017 | Godden et al. |
| 2017/0036032 A1 | 2/2017 | Schuler et al. |
| 2017/0112983 A1 | 4/2017 | Thorne et al. |
| 2017/0266371 A1 | 9/2017 | Leonhardt et al. |
| 2017/0274206 A1 | 9/2017 | Leonhardt |
| 2018/0043159 A1 | 2/2018 | Hassan et al. |
| 2018/0064935 A1 | 3/2018 | Leonhardt et al. |
| 2018/0071135 A1 | 3/2018 | Ingemarsson-Matzen |
| 2018/0193646 A1 | 7/2018 | Fostick et al. |
| 2019/0015661 A1 | 1/2019 | Leonhardt et al. |
| 2019/0022389 A1 | 1/2019 | Leonhardt |
| 2019/0022396 A1 | 1/2019 | Leonhardt |
| 2019/0125932 A1 | 5/2019 | Leonhardt et al. |
| 2019/0255321 A1 | 8/2019 | Planard-Luong |
| 2019/0290541 A1 | 9/2019 | Greiner et al. |
| 2020/0030136 A1 | 1/2020 | Hernandez |
| 2020/0121984 A1 | 4/2020 | Sama |
| 2020/0289826 A1 | 9/2020 | Leonhardt |
| 2020/0324106 A1 | 10/2020 | Leonhardt |
| 2020/0330753 A1 | 10/2020 | Leonhardt et al. |
| 2021/0228870 A1 | 7/2021 | Leonhardt |

FOREIGN PATENT DOCUMENTS

| | | |
|---|---|---|
| EP | 0603451 A1 | 6/1994 |
| GB | 2578310 A | 5/2020 |
| GB | 2578318 A | 5/2020 |
| JP | 2013-034881 A | 2/2013 |
| KR | 10-2007-0010908 A | 1/2007 |
| KR | 10-0726825 B1 | 6/2007 |
| WO | 92/17118 A1 | 10/1992 |
| WO | 2006/116728 A2 | 11/2006 |
| WO | 2007/146187 A2 | 12/2007 |
| WO | 2008/145724 A1 | 12/2008 |
| WO | 2009/021535 A1 | 2/2009 |
| WO | 2011/016629 A2 | 2/2011 |
| WO | 2014/172693 A2 | 10/2014 |
| WO | 2020/079436 A3 | 4/2020 |

OTHER PUBLICATIONS

Skardal "Amniotic Fluid Stem Cells for Wound Healing" Perinatal Stem Cells (Jul. 2014) Springer, New York, NY. https://doi.org/10.1007/978-1-4939-1118-9_2.

(56) References Cited

OTHER PUBLICATIONS

Skardal et al. "Bioprinted Amniotic Fluid-Derived Stem Cells Accelerate Healing of Large Skin Wounds" Stem Cells Translationalmedicine (Oct. 2012)1:792-802.
Su et al. "Klotho protein lowered in elderly hypertension" Int J Clin Exp Med (Aug. 2014) 7(8):2347-2350.
Sun "Regulation of Blood Pressure by Klotho" University of Oklahoma Health Sciences Center, Oklahoma City, OK, United States; accessed Jun. 2, 2021; https://grantome.com/grant/NIH/R01-HL102074-01A1.
Sun et al. "Amniotic fluid stem cells provide considerable advantages in epidermal regeneration: B7H4 creates a moderate inflammation microenvironment to promote wound repair" Scientific Reports (Jun. 2015) 5:11560, DOI: 10.1038/srep11560.
Sutherland et al. "Prolonged electrical stimulation of the nipples evokes intermittent milk ejection in the anaesthetised lactating rat," Exp Brain Res. 1987;66(1):29-34.
Takenaka et al. "Klotho Supplementation Attenuatesblood Pressure and Cyst Growth Inmouse Polycystic Kidney Disease" Journal of Hypertension: vol. 36—Issue—p. e76 (Jun. 2018).
Tyler "Nature's Electric Potential: A Systematic Review of the Role of Bioelectricity in Wound Healing and Regenerative Processes in Animals, Humans, and Plants" Front. Physiol., (Sep. 2017) https://doi.org/10.3389/fphys.2017.00627.
Ueland et al. "Inflammatory cytokines as biomarkers in heart failure," Clinica Chimica Acta, vol. 443, Mar. 30, 2015, pp. 71-77; doi.org/10.1016/j.cca.2014.09.001.
Vig et al. "Advances in Skin Regeneration Using Tissue Engineering" Int. J. Mol. Sci. (Apr. 2017), 18, 789; doi:10.3390/ijms18040789.
Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/S41551-017-0157-y.
Wei et al. "Nanofat-derived stem cells with platelet-rich fibrin improve facial contour remodeling and skin rejuvenation after autologous structural fat transplantation" Research Paper, Oncotarget (Jul. 2017) vol. 8, (No. 40), pp. 68542-68556.
Wu et al. "MSC-exosome: A novel cell-free therapy for cutaneous regeneration" Cytotherapy, vol. 20, Issue 3, (Mar. 2018) pp. 291-301, https://www.sciencedirect.com/science/article/pii/S146532491730717X.
Xiong et al. "Current understanding of neuroinflammation after traumatic brain injury and cell-based therapeutic opportunities" Chin J Traumatol. Jun. 2018; 21(3): 137-151. doi: 10.1016/j.cjtee.2018.02.003.
Yang et al. "Effect of Amniotic Fluid Stem Cells and Amniotic Fluid Cells on the Wound Healing Process in a White Rat Model" APS, vol. 40, No. 5 (Sep. 2013).
Yildirimer et al. "Skin regeneration scaffolds: a multimodal bottom-up approach" Trends in Biotechnology, Dec. 2012, vol. 30, No. 12, pp. 638-648.
Yoon et al. "Skin Regeneration Effect and Chemical Composition of Essential Oil from Artemisia montana" Natural Product Communications (Sep. 2014) vol. 9, No. 11, pp. 1619-1622.
Yu et al. "Effects and mechanisms of a microcurrent dressing on skin wound healing: a review" Military Medical Research (Nov. 2014) 1:24 http://www.mmrjournal.org/content/1/1/24.
Yuan et al. "Electrical stimulation enhances cell migration and integrative repair in the meniscus" Sci Rep 4, 3674 (2014). https://doi.org/10.1038/srep03674.
Zaske "Discovery enables adult skin to regenerate like a newborn's" Medical Research, accessed Aug. 4, 2021 https://medicalxpress-com.cdn.ampproject.org/c/s/medicalxpress.com/news/2020-09-discovery-enables-adult-skin-regenerate.amp.
Zhang et al. "Therapeutic potential of stem cells in skin repair and regeneration" Chinese Journal of Traumatology (Apr. 2008) 11(4):209-221.
Zhong et al. "TKI-31 inhibits angiogenesis by combined suppression signaling pathway of VEGFR2 and PDGFRbeta" Cancer Biology & Therapy 5:3, 323-330, Mar. 2006.
Zhou et al. "Klotho Ameliorates Kidney Injury and Fibrosis and Normalizes Blood Pressure by Targeting the Renin-Angiotensin System" The American Journal of Pathology, vol. 185, No. 12, Dec. 2015.
Zhou et al. "Klotho Gene Deficiency Causes Salt-Sensitive Hypertension via Monocyte Chemotactic Protein-1/CC Chemokine Receptor 2-Mediated inflammation" J Am Soc Nephrol 26: 121-132, 2015 (Accepted Apr. 2014).
Zimmerman et al. "Cancer cell proliferation is inhibited by specific modulation frequencies" Br J Cancer. Jan. 17, 2012;106(2):307-13. doi: 10.1038/bjc.2011.523. Epub Dec. 1, 2011. PMID: 22134506; PMCID: PMC3261663.
Zimmerman et al. "Targeted treatment of cancer with radiofrequency electromagnetic fields amplitude-modulated at tumor-specific frequencies" Chin J Cancer. Nov. 2013;32(11):573-81. doi: 10.5732/cjc.013.10177. PMID: 24206915; PMCID: PMC3845545.
Zhao et al. "Local osteoprotegerin gene transfer inhibits relapse of orthodontic tooth movement." Am J Orthod Dentofacial Orthop. Jan. 2012; 141(1):30-40. doi: 10.1016/j.ajodo.2011.06.035.
Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
Dahm et al. "Decalcification of the aortic valve does not prevent early recalcification" J Heart Valve Dis., 9(1):21-6 (Jan. 2000).
Ghazalian et al. "Effects of whole-body vibration training on fibrinolytic and coagulative factors in healthy young men." Journal of Research in Medical Sciences: the official journal of Isfahan University of Medical Sciences vol. 19,10 (Oct. 2014): 982-986.
Mei al. "Combined effect of rhTGF-ß1 and rhPDGF-BB on the expression of Pyk2 protein and mRNA gene during orthodontic tooth movement in SD rats" Shanghai Kou Qiang Yi Xue. Oct. 2019;28(5):472-477. Chinese. PMID: 32274476.
Messas et al. "Feasibility and Performance of Noninvasive Ultrasound Therapy in Patients With Severe Symptomatic Aortic Valve Stenosis: A First-in-Human Study. Circulation" Mar. 2, 2021;143(9):968-970. doi: 10.1161/CIRCULATIONAHA.120.050672. Epub Jan. 25, 2021.
Petrusca et al. "Experimental investigation of thermal effects in HIFU-based external valvuloplasty with a non-spherical transducer, using high-resolution MR thermometry" Phys Med Biol. Sep. 7, 2009;54(17):5123-38. doi: 10.1088/0031-9155/54/17/004. Epub Aug. 6, 2009 (ABSTRACT).
Shimamura et al. "OPG/RANKL/RANK axis is a critical inflammatory signaling system in ischemic brain in mice." Proceedings of the National Academy of Sciences of the United States of America vol. 111,22 (2014): 8191-6. doi:10.1073/pnas.1400544111.
Tsang et al. "Large animal models of cardiovascular disease" Cell Biochemistry and Function (Feb. 2016) vol. 34, Issue 3 p. 113-132.
Villemain et al. Pulsed Cavitational Ultrasound Softening : A New Noninvasive Therapeutic Approach for Calcified Bioprosthetic Valve Stenosis JACC: Basic to Translational Science vol. 2, Issue 4, Aug. 2017, pp. 372-383.
Westermark et al. "Effect of externally applied focused acoustic energy on clot disruption in vitro" Clinical Science 97(1):67-71 (Jul. 1999); DOI: 10.1042/CS19980379.
Wu et al. "Validation study toward measuring the mechanical properties of blood clots using resonant acoustic spectroscopy with optical vibrometry." Proceedings of SPIE—the International Society for Optical Engineering vol. 8214 (epub Feb. 2012): 82140G. doi:10.1117/12.906956.
Liebano et al. "Vascular Endothelial Growth Factor Release Following Electrical Stimulation in Human Subjects" Advances in Wound Care, vol. 3, No. 2, pp. 98-103 (Jun. 2013).
Morimoto et al. "Electrical Stimulation Enhances Migratory Ability of Transplanted Bone Marrow Stromal Cells in a Rodent Ischemic Stroke Model" Cell Physiol Biochem (Dec. 2018) 46:57-68.
Spadaccio et al. "In Situ Electrostimulation Drives a Regenerative Shift in the Zone of Infarcted Myocardium" Cell Transplantation, vol. 21, pp. 493-503, 2013 (Final Acceptance Mar. 2012).

(56) References Cited

OTHER PUBLICATIONS

Silva et al., "Analgesia Induced by 2- or 100-Hz Electroacupuncture in the Rat Tail-Flick Test Depends on the Activation of Different Descending Pain Inhibitory Mechanisms", The Journal of Pain, vol. 12, No. 1, Jan. 2011. (Year: 2011).

Dong-Hwan Kim et al., The effects of electrical current from a micro-electrical device on tooth movement, Korean Orthod., Oct. 2008, 38(5):337-346.

Ehrlich et al., "Engineering Approaches for the Detection and Control of Orthopaedic Biofilm Infections," Clinical Orthopaedics and Related Research, vol. 437, (2005), pp. 59-66.

El-Bialy et al. "Effect of Low Intensity Pulsed Ultrasound (LIPUS) on Tooth Movement and Root Resorption: A Prospective Multi-Center Randomized Controlled Trial" J. Clin. Med. 2020, 9, 804; doi:10.3390/jcm9030804.

Elastatropin(Registered) in Scalp & Hair Conditioning https://www.proteingenomics.com/haircare.html, Jun. 29, 2015.

Electric Tumor Treatment Fields, No. 0827 Policy, http://www.aetna.com/cpb/medical/data/800_899/0827.html (Nov. 18, 2016).

Electrical brain stimulation could support stroke recovery https://www.sciencedaily.com/releases/2016/03/160316151108.htm (Mar. 16, 2016).

Ellis, Marie "Cure for baldness? Stem cells bring hope" http://www.medicalnewstoday.com/articles/271898.php, Nov. 30, 2016.

Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.

Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.

Fatemi et al. "Imaging elastic properties of biological tissues by low-frequency harmonic vibration" Proceedings of the IEEE, 91(10):1503-1519 (Oct. 2003).

FDA Approves Algovita Spinal Cord Stimulation System from Greatbatch, http://www.odtmag.com/contents/view_breaking-news/2015-12-02/fda-approves-algovita-spinal-cord-stimulation-system-from-greatbatch (Dec. 2, 2015).

Fili et al. "Therapeutic implications of osteoprotegerin" Cancer Cell International vol. 9, Article No. 26 (2009).

Flachskampf et al., "Randomized Trial of Acupuncture to Lower Blood Pressure," Circulation, vol. 115, (2007), pp. 3121-3129.

Fonseca et al. "Electrical stimulation: Complementary therapy to improve the performance of grafts in bone defects?" Journal of Biomedical Materials Research Part B: Applied Biomaterials 2018 vol. 000b, Issue 0.

Froughreyhani et al., "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.

Fukuoka et al. "Hair Regeneration Treatment Using Adipose-Derived Stem Cell Conditioned Medium: Follow-up With Trichograms" Eplasty, 15:e10 (Mar. 2015).

Fukuoka et al., "The Latest Advance in Hair Regeneration Therapy Using Proteins Secreted by Adipose-Derived Stem Cells" The American Journal of Cosmetic Surgery, 29(4):273-282 (2012).

Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26(4):671-80.

Giladi et al., "Microbial Growth Inhibition by Alternating Electric Fields," Antimicrobial Agents and Chemotherapy, vol. 52, (2008), pp. 3517-3522.

Golberg et al., "Eradication of Multidrug-Resistant A. Baumannii in Burn Wounds by Antiseptic Pulsed Electric Field," Technology, vol. 2, (2014), pp. 153-160.

Golberg et al., "Pulsed Electric Fields For Burn Wound Disinfection in a Murine Model," Journal of Burn Care & Research, vol. 36, (2015), pp. 7-13.

Goranov et al. "Bone Lesions in Multiple Myeloma—The OPG/RANK-ligand System" Folia Med (Plovdiv). 2004; 46(3): 5-11 (Abstract Only).

Goswami et al. "Osteoprotegerin rich tumor microenvironment: implications in breast cancer" Oncotarget. Jul. 5, 2016; 7(27): 42777-42791.

Grad, D., "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).

Greenwald "Pulse pressure and arterial elasticity" QJM: An International Journal of Medicine, vol. 95, Issue 2, 2002, pp. 107-112.

Guimarães-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.

Gurbax et al. "Accelerated Orthodontic Tooth Movement: A Review" mod Res Dent. 1(2). MRD.000508. 2017. DOI: 10.31031/MRD.2017.01.000508.

Hair Growth Factors, Nanogen, http://www.svijet-kose.com/dokumenti/Serum-vegf.pdf, (2010).

Hamman, R. "Modulation Of RANKL and Osteoprotegerin in Adolescents Using Orthodontic Forces", Masters Thesis, University of Tennessee (2010).

Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.

Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.

Hart, K. "RANKL and Osteoprotegerin Levels in Response to Orthodontic Forces" (2012). Theses and Dissertations (ETD). Paper 107. http://dx.doi.org/10.21007/etd.cghs.2012.0127.

Healthcmi, "Acupuncture Combats Hypertension In University of California Research," Available online at < https://www.healthcmi.com/Acupuncture-Continuing-Education-News/1688-acupuncture-c . . . >, (2016), 9 pages.

Healthcmi, "Acupuncture Controls Hypertension In Groundbreaking Trial," Available online at < https://www.healthcmi.com/Acupuncture-Continuing-Education-News/1804-acupuncture-c . . . >, (2017), 9 pages.

Healthcmi, "UC Irvine—Acupuncture Reduces Hypertension Confirmed," Available Online at < https://www.healthcmi.com/Acupuncture-Continuing-Education-News/1792-uc-irvine-acup . . . >, (2017), 6 pages.

Heart Valve Calcifications—Focused Ultrasound TherapyFocused Ultrasound Therapy; Research Paper Last Updated: Jan. 28, 2020, The Focused Ultrasound Foundation Newsletter (5 pages).

Hearts build new muscle with this simple protein patch, jacobsschool.ucsd.edu/news/news_releases/release.sfe?id=1813(Sep. 16, 2015).

HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).

Hoffmann, "Regeneration of the gastric mucosa and its glands from stem cells", Curr Med Chem, 15(29):3133-44 (2008).

Holding et al. "The correlation of RANK, RANKL and TNFa expression with bone loss volume and polyethylene wear debris around hip implants" Biomaterials 27(30):5212-9—Nov. 2006.

Holen et al. "Role of Osteoprotegerin (OPG) in Cancer" Clin Sci (Lond). Mar. 2006; 110(3):279-91. doi: 10.1042/CS20050175.

Hopkins Medicine "Overview of Pacemakers and Implantable Cardioverter Defibrillators (ICDs)," hopkinsmedicine.org/healthlibrary/conditions/cardiovascular_diseases/ )verview of pacemakers and implantable cardioverter defibrillators icds 85,P00234/, last visited Sep. 12, 2018.

https://www.dicardiology.com/content/bioleonhardt-unveils-stem-pump Jan. 28, 2014.

Hu et al. "Klotho Deficiency Causes Vascular Calcification in Chronic Kidney Disease" J Am Soc Nephrol. Jan. 2011; 22(1): 124-136.

HU Klein, "Vagus Nerve Stimulation: A new approach to reduce heart failure" Cardiology Journal (2010).

(56) References Cited

OTHER PUBLICATIONS

Huang et al. "Myocardial transfection of hypoxia-inducible factor-1a and co-transplantation of mesenchymal stem cells enhance cardiac repair in rats with experimental myocardial infarction", Stem Cell Research & Therapy 5:22 (2014) DOI: 10.1186/scrt410.
Hudson et al. "Local delivery of recombinant osteoprotegerin enhances postorthodontic tooth stability" Calcif Tissue Int. Apr. 2012; 90(4):330-42. doi: 10.1007/S00223-012-9579-4.
Hy et al., "Insulin-like growth factor 1 and hair growth," Dermatol Online J,; 5(2):1 (Nov. 1999).
Iglesias-Linares et al. "The use of gene therapy vs. corticotomy surgery in accelerating orthodontic tooth movement." Orthod Craniofac Res. Aug. 2011; 14(3):138-48. doi: 10.1111/j.1601-6343.2011.01519.x.
Infante et al. "RANKL/RANK/OPG system beyond bone remodeling: involvement in breast cancer and clinical perspectives" Journal of Experimental & Clinical Cancer Research (2019) 38:12. https://doi.org/10.1186/s13046-018-1001-2.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
"Electric Tumor Treatment Fields," No. 0827 Policy, aetna.com/cpb/medical/data/800_899/0827.html (Nov. 18, 2016), last visited Sep. 12, 2018.
"Electrical brain stimulation could support stroke recovery," sciencedaily.com/releases/2016/03/160316151108.htm (Mar. 16, 2016), last visited Sep. 12, 2018.
"FDA Approves Algovita Spinal Cord Stimulation System from Greatbatch," http://www.odtmag.com/contents/view_breaking-news/2015-12-02/fda-approves-algovita-spinal-cord-stimulation-jystem-from-greatbatch (Dec. 2, 2015).
Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.
Almpani et al., "Nonsurgical Methods for the Acceleration of the Orthodontic Tooth Movement", Tooth Movement. Front Oral Biol., vol. 18, pp. 80-91 (Karger, Basel, CH 2016) (DOI: 10.1159/000382048), Published online: Nov. 24, 2015.
Ando et al." RANKL/RANK/OPG: key therapeutic target in bone oncology" Curr Drug Discov Technol. Sep. 2008; 5(3): 263-268.
Atkinson et al. "Bioelectric Properties of the Tooth" 1969 vol. 48 issue: 5, pp. 789-794.
Aubert et al. "A new ultrasonic process for a renewal of aortic valve decalcification" Cardiovascular Ultrasound 2006, 4:2 doi:10.1186/1476-7120-4-2.
Aydin et al., "Focusing of Electromagnetic Waves by a Left-Handed Metamaterial Flat Lens," vol. 13, (2005), pp. 8753-8759.
Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 vol. 5 | Article 196.
Banerjee, P. "Electrical muscle stimulation for chronic heart failure: an alternative tool for exercise training?" Curr Heart Fail Rep., 7(2):52-8. doi: 10.1007/s11897-010-0013-9 (Jun. 2010).
Bang et al., "Attenuation of Hypertension by C-Fiber Stimulation of the Human Median Nerve and the Concept-Based Novel Device," Scientific Reports, vol. 8, (2018), 12 pages.
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
Barker et al., "A Formidable Foe is Sabotaging Your Results: What You Should Know About Biofilms and Wound Healing," Plastic and Reconstructive Surgery, vol. 139, (2017), pp. 1184e-1194e.
Beitelshees et al. "CXCL5 polymorphisms are associated with variable blood pressure in cardiovascular disease-free adults" Hum Genomics. 2012; 6(1): 9.
Bi et al. "Key Triggers of Osteoclast-Related Diseases and Available Strategies for Targeted Therapies: A Review" Front Med (Lausanne). 2017; 4: 234. doi: 0.3389/fmed.2017.00234.
Blood Vessels Hold Key To Thicker Hair Growth, https://www.sciencedaily.com/releases/2001/02/010215074636.htm(Feb. 2001).
Borden et al., "Electric Current-Induced Detachment of *Staphylococcus epidermidis* Biofilms from Surgical Stainless Steel," Applied and Environmental Microbiology, vol. 70, (2004), pp. 6871-6874.
Borgobello, B. "FDA approves the treatment of brain tumors with electrical fields," New Atlas, http://newatlas.com/treatment-of-brain-tumors-with-electrical-fields/21433/(Feb. 13, 2012), last visited Sep. 12, 2018.
Bradshaw et al. "Designer self-assembling hydrogel scaffolds can impact skin cell proliferation and migration" Nature Scientific Reports, vol. 4, Article No. 6903 (2014).
Brooks et al. "Bioelectric impedance predicts total body water, blood pressure, and heart rate during hemodialysis in children and adolescents" J. Ren Nutr., 18(3):304-311 (May 2008); doi: 10.1053/j.jrn.2007.11.008.
Buckle et al. "Soluble Rank Ligand Produced by Myeloma Cells Causes Generalised Bone Loss in Multiple Myeloma" PLoS One. 2012; 7(8): e41127. doi: 10.1371/journal.pone.0041127 PMCID: PMC3430669.
Cai et al., "Intermedin Inhibits Vascular Calcification by Increasing the Level of Matrix (Gamma)-Carboxyglutamic Acid Protein," Cardiovascular Research, vol. 85, (2010), pp. 864 873.
Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.
Caubet et al., "A Radio Frequency Electric Current Enhances Antibiotic Efficacy Against Bacterial Biofilms," Antimicrobial Agents and Chemotherapy, vol. 48, (2004), vol. 4662-4664.
Cerrada et al. "Hypoxia-Inducible Factor 1 Alpha Contributes to Cardiac Healing in Mesenchymal Stem Celis-Mediated Cardiac Repair," Stem Cells and Development, 22(3): 501-511 (2013).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Chang et al. Effect of Pulse-Burst Electromagnetic Field Stimulation on Osteoblast Cell Activities; Bioelectromagnetics 25:457-465 (2004).
Chemet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA.117.10560.) Downloaded from http://ahajournals.org by on Apr. 24, 2020 (9 pages).
Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Chen et al., "The Role and Mechanism of (Alpha)-Klotho in the Calcification of Rat Aortic Vascular Smooth Muscle Cells," BioMed Research International, vol. 2015, (2015), 7 pages.
Chen et al., "The Strategy to Prevent and Regress the Vascular Calcification in Dialysis Patients," BioMed Research International, vol. 2017, (2017), 11 pages.
Chen et al., Efficacy and Safety of Acupuncture for Essential Hypertension: A Meta-Analysis, Medical Science Monitor, vol. 24, (2018), pp. 2946-2969.
Chiang et al., "Silver-Palladium Surfaces Inhibit Biofilm Formation," Applied and Environmental Microbiology, vol. 75, (2009), pp. 1674-1678.

(56) References Cited

OTHER PUBLICATIONS

Christouls et al. "Pathogenesis and Management of Myeloma Bone Disease" Expert Rev Hematol. 2009; 2(4):385-398.
Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830>, 1 page. (Abstract Only).
Collins "Bioelectric Signals Can Be Used to Detect Early Cancer," Tufts News, http://now.tufts.edu/news-releases/bioelectric-signals-used-detect-early-cancer (Feb. 1, 2013).
Columbia "Implant Procedure Concepts—Pacemaker, ICD and CRT Overview," columbia.edu/itc/hs/medical/hickey/docs/Pacemaker,%20ICD%20and%20CRT%200verview%20022007.pdf, last risited Sep. 12, 2018.
Control of Hair Growth by a Growth Factor Protein, http://www.hairloss-reversible.com/control-of-hair-growth-by-a-growth-factor-protein/, Nov. 17, 2016.
Control of pelage hair follicle development and cycling by complex interactions between follistatin and activin, FASEB J (Jan. 2, 2003).
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Costerton et al., "The Application of Biofilm Science to the Study and Control of Chronic Bacterial Infections," The Journal of Clinical Investigation, vol. 112, (2003), pp. 1466-1477.
Cowburn et al. "HIF isoforms in the skin differentially regulate systemic arterial pressure" Proc Natl Acad Sci U S A. Oct. 22, 2013; 110(43): 17570-17575.
Delcaru et al., "Microbial Biofilms in Urinary Tract Infections and Prostatitis: Etiology, Pathogenicity, and Combating slialegies," Pathogens, vol. 5, (2016), 12 pages.
Dibart et al. "Tissue response during Piezocision-assisted tooth movement: a histological study in rats", Eur J Orthod (2014) 36 (4): 457/\64; DOI: https://doi.org/10.1093/ejo/cjt079.
Dietrich et al. "Decalcification of the mitral annulus: surgical experience in 81 patients" Thorac Cardiovasc Surg. Oct. 2006;54(7):464-7 (Abstract Only).
McLean et al., "Training the Biofilm Generation—a Tribute to J. W. Costerton," Journal of Bacteriology, vol. 194, (Dec. 2012), pp. 6706-6711.
Medtronic "Cardiac Resynchronization Therapy (CRT) Devices For Heart Failure" http://www.medtronic.com/us-en/patients/treatments-therapies/crt-devices.html, Feb. 15, 2017.
Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).
Moe, "Klotho: A Master Regulator of Cardiovascular Disease?," Circulation, vol. 125, (2012), pp. 2181-2183.
Mosteiro et al. "Tissue damage and senescence provide critical signals for cellular reprogramming in vivo." Science, 2016; 354 (6315): aaf4445 DOI: 10.1126/science.aaf4445.
Niiranen et al., "Relative Contributions of Arterial Stiffness and Hypertension to Cardiovascular Disease: The Framingham Heart Study," Journal of the American Heart Association, vol. 5, No. 11, 2016, 8 pages.
Nimeri et al. "Acceleration of tooth movement during orthodontic treatment—a frontier in Orthodontics", Prog Orthod 2013; 14:42; DOI: 10.1186/2196-1042-14-42.
Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.
Nordstorm "Electrical Stimulation Blood Pressure Treatment Devices Market to Set Astonishing Growth by 2026" Art. Apr. 4, 2019 Gator Ledger.
Norton et al. "Bioelectric Perturbations of Bone: Research Directions and Clinical Applications" Angle Orthod (1984) 54 (1): 73-87.
Novack "Inflammatory osteoclasts, a different breed of bone eaters?" Arthritis Rheumatol. Dec. 2016; 68(12): 2834-2836. doi: 10.1002/art.39835.
Novickij et al., "Induction of Different Sensitization Patterns of MRSA to Antibiotics Using Electroporation," Molecules, vol. 23,(2018), Article 1799, 10 pages.
O'Neill et al., "Recent Progress in the Treatment of Vascular Calcification," Kidney International, vol. 78, (Dec. 2010), pp. 1232-1239.
Oranger et al. "Cellular Mechanisms of Multiple Myeloma Bone Disease" Clinical and Developmental Immunology vol. 2013, Article ID 289458, 11 pages http://dx.doi.org/10.1155/2013/289458.
Otero et al. "Expression and Presence of OPG and RANKL mRNA and Protein in Human Periodontal Ligament with Orthodontic Force", Gene-Regulation-and-Systems-Biology, 2016, 10, 15-20.
Our Approach to Improve Hair Loss by Increasing Hair Growth Factor IGF-1, http://www.jhgc.com.sg/theory/igf-1/index.html, Jul. 7, 2014.
Oyajobi "Multiple myeloma/hypercalcemia" Arthritis Research & Therapy vol. 9, Article No. S4 (2007).
Palza et al., "Electroactive Smart Polymers for Biomedical Applications," Materials, vol. 12, (2019), 24 pages.
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
Park, Alice "Shrinking Stem Cells Are the Real Reason for Hair Loss" Time, (Feb. 5, 2016).
Pierce et al. "Collection and characterization of amniotic fluid from scheduled C-section deliveries," Cell Tissue Bank, DOI 10.1007/s10561-016-9572-7 (Springer, 2012) and is available from Irvine Scientific.
Plumbingtoday, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.
Pozo et al., "Bioelectric Effect and Bacterial Biofilms. A Systematic Review," The International Journal of Artificial Organs, vol. 31, (2008), pp. 786-795.
Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35-40.
Pozo et al., "Prevention of *Staphylococcus epidermidis* Biofilm Formation Using Electrical Current," Journal of Applied Biomaterials & Functional Materials, vol. 12, (2014), pp. 81-83.
Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.
Price et al. "Mitral Valve Repair is Feasible Following Extensive Decalcification and Reconstruction of the Atrioventricular Groove" J Heart Valve Dis. Jan. 2015;24(1):46-52 (Abstract Only).
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.
Raje et al. "Role of the RANK/RANKL Pathway in Multiple Myeloma" Clin Cancer Res 2019 25(1):12-20; DOI: 10.1158/1078-0432.CCR-18-1537.
Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.
Reversing Age-Related Hair Loss and Restoring Healthy Hair Growth in Men and Women https://nutritionreview.org/2015/08/

(56) References Cited

OTHER PUBLICATIONS reversing-age-related-hair-loss-and-restoring-healthy-hair-growth-in-men-and-women/ (Aug. 24, 2015).
Robert Ferris, "Battle against baldness turns to stem cells" http://www.cnbc.com/2015/01/29/studies-indicate-its-possible-to-use-stem-cells-to-cure-baldness.html (Jan. 29, 2015).
Roy et al., "Disposable Patterned Electroceutical Dressing (PED-10) Is Safe for Treatment of Open Clinical Chronic Wounds," Advances in Wound Care, vol. 8, pp. 149-159, (2019).
Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages) Abstract Only.
Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.
Sahoo and Losordo "Exosomes and Cardiac Repair After Myocardial Infarction," Circulation Research, 114:333-344 (Jan. 16, 2014).
Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).
Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.
Schardong et al., "Intradialytic neuromuscular electrical stimulation reduces DNA damage in chronic kidney failure patients: a randomized controlled trial," Biomarkers, vol. 23, Issue 5, 2018, pp. 1-11.
Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.
Scott Jeffrey, "How to Decalcify Your Pineal Gland (And Why It's Really Important for Higher Mental Performance)," (available at https://scottjeffrey.com/decalcify-your-pineal-gland/), Retrieved on May 23, 2019, 23 pages.
Seifi & Jeszri "Correlation of bone resorption induced by orthodontic tooth movement and expression of RANKL in rats", Dental Journal, vol. 26, No. 4 (2009).
Sethi et al. "Aortic stiffness: pathophysiology, clinical implications, and approach to treatment" Integr Blood Press Control. 2014; 7: 29-34.
Shahid et al., "Rhinosinusitis in Children," ISRN Otolaryngology, vol. 2012, Article ID 851831, (Dec. 2012), 11 pages.
Shirtliff et al., "Assessment of the Ability of the Bioelectric Effect to Eliminate Mixed-Species Biofilms," Applied and Environmental Microbiology, vol. 71, (2005), pp. 6379-6382.
Shoji-Matsunaga et al. "Osteocyte regulation of orthodontic force-mediated tooth movement via RANKL expression." Scientific Reports, 7: 8753, published online Aug. 18, 2017, DOI:10.1038/s41598-017-09326-7.
Showkatbakhsh et al. "Effect of Intra-Canal Direct Current Electric Stimulation on Orthodontic Tooth Movement: An Experimental Study in Canines" Journal of Dental School 2016; 34(3): 157-67.
Showkatbakhsh et al. "The effect of pulsed electromagnetic fields on the acceleration of tooth movement." World J Orthod. 2010 Winter;11(4):e52-6.
JCCR "Emerging roles of klotho in cardiovascular diseases%5D" Accessed Jun. 2, 2021 https://medcraveonline.com/JCCR/emerging-roles-of-klotho-in-cardiovascular-diseases.html%5D.
Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.
John et al. "Growth Factors in Skin Care—Series Introduction" (Mar. 2015) website accessed Aug. 4, 2021 http://barefacedtruth.com/2015/03/28/growth-factors-skin-care-introduction/.
John et al. "Growth Factors in Skin Care—Series Introduction" BareFacedTruth (Mar. 2015) 9 pages.
Jouybar et al. "Enhanced Skin Regeneration by Herbal Extract-Coaled Poly-L-Lactic Acid Nanofibrous Scaffold" Artif Organs. Nov. 2017; 41(11):E296-E307. doi: 10.1111/aor.12926 (Abstract Only).
Jung et al. "Prospective 1-Year Follow-Up Study of Breast Augmentation by Cell-Assisted Lipotransfer" Aesthetic Surgery Journal 2016, vol. 36(2) 179-190 © 2015 The American Society for Aesthetic Plastic Surgery, Inc.
Kawagishi et al. S"onic hedgehog signaling regulates the mammalian cardiac regenerative response" Journal of Molecular and Cellular Cardiology; vol. 123, p. 180-184 (Oct. 2018).
Keunen et al. "Anti-VEGF treatment reduces blood supply and increases tumor cell invasion in glioblastoma," Proc. Natl. Acad. Sci. U.S. A. Mar. 1, 2011; 108(9):3749-3754, published online Feb. 14, 2011; doi: 10.1073/pnas.1014480108.
Kim et al. "Hyaluronate—Epidermal Growth Factor Conjugate for Skin WoundHealing and Regeneration" Biomacromolecules (Oct. 2016) 17 , 11, 3694-3705 (Abstract Only) Publication Date : Oct. 24, 2016.
Kim et al. "Picking Winners and Losers: Cell Competition in Tissue Development and Homeostasis" vol. 36, Issue 7, p. 490-498, Jul. 1, 2020 (Abstract Only).
Lam et al. "Mesenchymal stem cell therapies for skin repair and regeneration" J Dermat Cosmetol. (Aug. 2017) vol. 1, Issue 3, pp. 62?64.
Landau et al. "Review: Proposed Methods to Improve the Survival of Adipose Tissue in Autologous Fat Grafting" Plast Reconstr Surg Glob Open. 2018;6(8):e1870. Published Aug. 3, 2018. doi:10.1097/GOX.0000000000001870.
Lanzetto et al. "Fundamental principles of an anti-VEGF treatment regimem optimal application of intravitreal anti-vascular endothelial growth factor therapy of macular diseases," Graefes Arch. Clin. Exp. Ophthalmol. 2017; 255(7)11259-1273 (published online May 19, 2017); doii 10.1007/s00417-017-3647-4.
Ledzewicz et al. "Analysis of optimal controls for a mathematical model of tumor anti-angiogenesis" Optim. Control Appl. Meth. 2006; 00:1-16.
Leonhardt "PressureStim Blood Pressure Control" accessed Jun. 2, 2021, https://pressurestim.com.
Leonhardt "PressureStim Receives IRB Approval to Launch Bioelectric Hypertension Treatment Clinical Study" Accessed Jun. 2, 2021, https://www.prdistribution.com/news/pressurestim-receives-irb-approval-to-launch-bioelectric-hypertension-treatment-clinical-study-2.html?fbclid=IwAR28Dh97RAKXXHrfgUONKW1pk-MWyeF_ibUIpQc_2XEN32C6sS%E2%80%A6.
Liesz et al. Editorial: Mechanisms of neuroinflammation and inflammatory neurodegeneration in acute brain injury Front. Cell. Neurosci., 2015. doi://doi.org/10.3389/fncel.2015.00300.
LifeWave X39™ Patches; website access Aug. 4, 2021 https://lifewave.com/corporphan/store/product/39000.022.009/.
Lobo-Silva et al. "Balancing the immune response in the brain: IL-10 and its regulation," Journal of Neuroinflammation, 13:297 (2016); doi.org/10.1186/s12974-016-0763-8.
Loizzi et al. "Biological Pathways Involved in Tumor Angiogenesis and Bevacizumab Based Anti-Angiogenic Therapy with Special References to Ovarian Cancer" International Journal of Molecular Sciences. (Sep. 2017); 18(9): 1967. https://doi.org/10.3390/ijms18091967.
Lopes-Bastos et al. "Tumour-Endothelial Cell Communications: Important and Indispensable Mediators of Tumour Angiogenesis" Anticancer Research Mar. 2016, 36 (3) 1119-1126.
Maltese et al. "The Putative Role of the Antiageing Protein Klotho in Cardiovascular and Renal Disease" Hindawi Publishing Corporation International Journal of Hypertension, (Sep. 2011) vol. 2012, Article ID 757469, 5 pages.
Mann, "Innate Immunity and the Failing Heart: The Cytokine Hypothesis Revisited," Circ. Res. Mar. 27, 2015; 116(7): 1254 1268.
Mao et al. "13-Hydrogel fibrous scaffolds for accelerated wound healing" In Woodhead Publishing Series in Biomaterials, Electrofluidodynamic Technologies (EFDTs) for Biomaterials and

(56) References Cited

OTHER PUBLICATIONS

Medical Devices, Woodhead Publishing, (Jan. 2018) pp. 251-274, ISBN 9780081017456, https://doi.org/10.1016/B978-0-08-101745-6.00013-X.
Matsumori, "Cytokines and Heart Failure: Pathophysiological Roles and Therapeutic Implications," Heart Failure, Springer, Tokyo; doi.org/10.1007/978-4-431-68331-5_3, (2000).
McMillan "Longevity Protein' Enables Muscle Regeneration In Old Mice" accesses Jun. 2, 2021; https://www.forbes.com/sites/fionamcmillan/2018/11/25/longevity-protein-enables-muscle-regeneration-in-old-mice/?sh=51709d57392a.
Meadows et al. "Anti-VEGF Therapies in the Clinic," Cold Spring Harb. Perspect. Med. Oct. 2012; 2(10): a006577: doi: 10.1101/cshperspect.a006577.
Metro News "Bioelectricity: A shocking revolution in skincare?" Website accessed Aug. 4, 2021 https://metro.co.uk/2010/09/26/bioelectricity-a-shocking-revolution-in-skincare-523763/.
Miron "The Concept of Smart Tissue Regeneration with PRF" (Apr. 3, 2017) accessed Aug. 4, 2021 http://oasisdiscussions.ca/2017/04/03/prf/.
Mishra "Angiogenic neovessels promote tissue hypoxia," Proc. Natl. Acad. Sci. U. S. A. Sep. 20, 2016; 113(38): 10458-10460, published online Sep. 13, 2016; doi: 10.1073/pnas.1612427113.
Muratori et al. "The cytotoxic synergy of nanosecond electric pulses and low temperature leads to apoptosis" Sci Rep 6, 36835 (2016). https://doi.org/10.1038/srep36835.
Nacopoulos "Use of Platelet Rich Fibrin in Facial Aesthetics and Rejuvenation" (Jun. 2017) accessed Aug. 4, 2021 https://doi.org/10.1002/9781119406792.ch 13.
Nature "Skin regeneration with insights" Nature 551, 141 (Nov. 2017) https://doi.org/10.1038/551141a.
Odell et al. "Anti-inflammatory Effects of Electronic Signal Treatment" Pain physician. 11.891-907 (2008). 10.36076/ppj.2008/11/891.
Ojeh et al. "Stem Cells in Skin Regeneration, Wound Healing, and Their Clinical Applications" Int. J. Mol. Sci. (Oct. 2015), 16, ISSN 1422-0067 www.mdpi.com/journal/ijms.
Paulus "Cytokines and heart failure," Heart Fail. Manit. 2000; 1 (2):50-6.
Payne et al. "Bioelectric Control of Metastasis in Solid Tumors" Bioelectricity vol. 1, No. 3, (Sep. 16, 2019) https://doi.org/10.1089/bioe.2019.0013.
Petrescu et al. "Platelet rich fibrin as a gingival tissue regeneration enhancer" Journal of Dental Sciences, https://doi.org/10.1016/j.jds.2020.08.014, Aug. 1, 2020.
Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from: http://www.intechopen.com/books/current-cancer-treatment-novel-beyond-conventional-approaches/electrotherapy-on-cancer-experiment-and-mathematical-modeling, 2011.
Puro et al "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.
RFA (radiofrequency ablation), Swedish Medical Imaging, 2 pages, author unknown, undated, (Sep. 2015).
Rocha et al. "Ultrasensitive System for Electrophysiology of Cancer Cell Populations: A Review" Bioelectricity vol. 1, No. 3 (Published Online:Sep. 16, 2019) https://doi.org/10.1089/bioe.2019.0020.
Ronchetti et al. "Dermal alterations in patients with Wilson's disease treated with D-penicillamine" J Submicrosc Cytol Pathol (Jan. 1989) 21(1 ):131-9.
Santos et al. "Interferential electrical stimulation improves peripheral vasodilatation in healthy individuals" Braz J Phys Ther. May-Jun. 2013; 17(3):281-288.
Sartori et al. "Effects of Transcutaneous Electrical Nerve Stimulation in Autonomic Nervous System of Hypertensive Patients: A Randomized Controlled Trial" Current Hypertension Reviews, Apr. 2018, 14, 66-71.
Schimmel et al. "Neuroinflammation in traumatic brain injury: A chronic response to an acute injury" Brain Circ, 2017, 3(3):135-142.
Segura et al. "New Material Developed for Accelerated Skin Regeneration in Major Wounds" National Institute of Biomedical Imaging and Bioengineering (Dec. 2015) Accessed Aug. 4, 2021 https://www.newswise.com/articles/new-material-developed-for-accelerated-skin-regeneration-in-major-wounds?channel=.
Silva et al. "Engineered hydrogel-based matrices for skin wound healing" (Dec. 2016) In book: Wound Healing Biomaterials (pp. 227-250) DOI:10.1016/B978-1-78242-456-7.00011-8.
Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.
Singh et al. "3D Printing of Scaffold for Cells Delivery: Advances in Skin Tissue Engineering" Polymers (Jan. 2016), 8, 19; doi:10 3390/polym8010019.
Interesting study about prolactin, VEGF and angiogenic inhibition, http://www.regrowth.com/hair-loss-forums/topic/interesting-study-about-prolactin-vegf-and-angiogenic-inhibition/ (Nov. 2006).
International Search Report for International Application No. PCT/US19/52288, dated Jan. 10, 2020, 11 pages.
International Written Opinion for International Application No. PCT/US19/52288, dated Jan. 10, 2020, 07 pages.
Involvement of hepatocyte growth factor/scatter factor and Met receptor signaling in hair follicle morphogenesis and cycling, FASEB J Feb. 2000 14:319-332.
Israeli innovation uses nerve stimulation to treat heart failure https://www.israel21c.org/israeli-innovation-uses-nerve-stimulation-to-treat-heart-failure/ (Feb. 11, 2007).
Istanbullu et al., "Electrochemical Biofilm Control: Mechanism of Action," Biofouling, vol. 28, (2012), pp. 769-778.
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Jia et al., "Activin B Promotes Initiation and Development of Hair Follicles in Mice" Cells Tissues Organs, 198:318-326 (Feb. 2014).
Kanno et al., Establishment of a Simple and Practical Procedure Applicable to Therapeutic Angiogenesis, Circulation, 1999, pp. 2682-2687, vol. 99.
Kanzaki et al. "Local OPG gene transfer to periodontal tissue inhibits orthodontic tooth movement." J Dent Res 2004; 83:92/925.
Kanzaki et al. "Local RANKL gene transfer to the periodontal tissue accelerates orthodontic tooth movement", Gene Therapy, (2006) 13, 678-685.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.
Kasimanickam et al., "Prevention and Treatment of Biofilms by Hybrid- and Nanotechnologies," International journal of Nanomedicine, vol. 8, (2013), pp. 2809-2819.
Kaur et al. "Electrically conductive polymers and composites for biomedical applications", RSC Adv., 2015,5, 37553-37567 DOI: 10.1039/C5RA01851J.
Keles et al. "Inhibition of tooth movement by osteoprotegerin vs. pamidronate under conditions of constant orthodontic force", Eur J Oral Sci. Apr. 2007;115(2):131-6.
Khan et al. "Accelerating Tooth Movement: What Options We Have?" J Dent Health Oral Disord Ther 2016, 5(7): 00181.
Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.
Kim et al., "Effect of Electrical Energy on the Efficacy of Biofilm Treatment Using the Bioelectric Effect," NPJ Biofilms and Microbiomes, vol. 1, (2015), Article 15016, 8 pages.
Kim et al., The effects of electrical current from a micro-electrical device on tooth movement, http://e-kjo.org/search.php?where=aview &id=10.4041/kjod.2008.38.5.337& . . . visited Aug. 2, 2017.

(56) References Cited

OTHER PUBLICATIONS

King et al. "Mechanical Decalcification of the Aortic Valve" 272 The Annals of Thoracic Surgery vol. 42 No. 3 Sep. 1986 (pp. 269-272).

Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.

Kondo et al. "Types of tooth movement, bodily or tipping, do not affect the displacement of the tooth's center of resistance but do affect the alveolar bone resorption" Angle Orthod Jul. 2017; 87(4):563-569.

Kose et al. "Citric acid as a decalcifying agent for the excised calcified human heart valves" Anadolu Kardiyol Derg 2008; 8: 94-8 (Eng Abstract).

Krishnan et al. (eds.), "Biological Mechanisms of Tooth Movement", John Wiley & Sons 2015 (10 pages).

Lamoureux et al. "Therapeutic Relevance of Osteoprotegerin Gene Therapy in Osteosarcoma: Blockade of the Vicious Cycle between Tumor Cell Proliferation and Bone Resorption" Cancer Res 1 2007 67(15):7308-7318; DOI: 10.1158/0008-5472.CAN-06-4130.

Lasserre et al., "Influence of Low Direct Electric Currents and Chlorhexidine Upon Human Dental Biofilms," Clinical and Experimental Dental Research, vol. 2, (Jul. 2016), pp. 146-154.

Lasserre et al., "Oral Microbes, Biofilms and Their Role in Periodontal and Peri-Implant Diseases," Materials, vol. 11, (Sep. 2018), Article 1802, 17 pages.

Lee et al. "Hepatocyte growth factor (HGF) activator expressed in hair follicles is involved in in vitro HGF-dependent hair follicle elongation," J. Dermatol. Sci., 25(2):156-63 (Feb. 2001).

Lee et al., "Targeted Release of Tobramycin From a pH-Responsive Grafted Bilayer Challenged With *S. aureus*," Biomacromolecules, vol. 16, (2015), pp. 650-659.

Lei et al., "Efficacy of Reversal of Aortic Calcification by Chelating Agents," Calcified Tissue International, vol. 93, (Nov. 2013), 15 pages.

Leibrock et al., "NH4Cl Treatment Prevents Tissue Calcification in Klotho Deficiency," Journal of the American Society of Nephrology, vol. 26, (2015), pp. 2423-2433.

Leonhardt "Micro Stimulator" http://www.bioleonhardt.com/micro-stimulator/, (2012).

Leonhardt "Leonhardt Adds HIF-1 Alpha To Estate of Bioelectric Controlled Release Regenerative Proteins" Press Release, Published Jun. 13, 2017.

Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.

Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.

Martin "Historically significant events in the discovery of RANK/RANKL/OPG" World J Orthop. Oct. 18, 2013; 4(4): 186-197. doi: 10.5312/wjo.v4.i4.186.

Mass Device "Greatbatch wins FDA PMA for Algovita SCS" http://www.massdevice.com/greatbatch-wins-fda-pma-for-algovita-scs/ (Dec. 1, 2015).

McBride et al. "Aortic valve decalcification" J Thorac Cardiovasc Surg. Jul. 1990;100(1):36-42; discussion 42-3 (Abstract Only).

McGrath "OPG/RANKL/RANK Pathway as a Therapeutic Target in Cancer" Journal of Thoracic Oncology, Sep. 2011 6(9): 1468-1473.

Abdel-Rehim "Change of serum klotho protein and its relationship with endothelial dysfunction, oxidative stress and arterial aging in essential hypertensive patients" J Kidney 2018, vol. 4 (Dec. 2018).

Ahrens et al. "Klotho expression is a prerequisite for proper muscle stem cell function and regeneration of skeletal muscle" Ahrens et al. Skeletal Muscle (Jul. 2018) 8:20 pp. 1-14.

Akbari Ei Al. "Association of Klotho gene polymorphism with hypertension and coronary artery disease in an Iranian population" BMC Cardiovascular Disorders (Dec. 2018) 18:237.

Andersson et al. "Drinking, antidiuresis and milk ejection from electrical stimulation within the hypothalamus of the goat," Acta Physiol Scand. Dec. 31, 1955; 35(2):191-201; DOI: 10.1111/j.1748-1716.1955.tb01277.x.

Aronowitz et al. "Mechanical versus enzymatic isolation of stromal vascular fraction cells from adipose tissue" SpringerPlus (2015) 4:713 DOI 10.1186/s40064-015-1509-2.

ASPS, "Stem Cell Treatments 'Go Deep' to RegenerateSun-Damaged Skin" Article, American Society of Plastic Surgeons (May 27, 2020) 4 pages.

Banerjee et al. "MicroRNAs in Skin and Wound Healing" Methods Mol Biol. 2013; 936: 343-356, Author manuscript (Mar. 2015).

Barnhill "It's Electric! All About Microcurrent Facials" accessed Aug. 4, 2021, https://intothegloss.com/2016/04/microcurrent-treatment/.

Basu et al. "Exosomes for repair, regeneration and rejuvenation" Expert Opinion on Biological Therapy, 16:4, 489-506, DOI: 10.1517/14712598.2016.1131976, Dec. 12, 2015.

Beebe et al. "Bioelectric Applications for Treatment of Melanoma," Cancers (Basel). Sep. 2010; 2(3): 1731-1770, published online Sep. 27, 2010; doi: 10.3390/cancers20317.

Berman "Suzanne Somers' Experimental Breast Reconstruction" Medpage Today, Feb. 7, 2012, www.medpagetoday.com > blogs > celebritydiagnosis.

Beugels et al. "Electrical stimulation promotes the angiogenic potential of adipose-derived stem cells" Scientific Reports (Aug. 2019) 9:12076.

Blum "Role of cytokines in heart failure," American Heart Journal, vol. 135, Issue 2, Feb. 1998, pp. 181-186; doi.org/10.1016/S0002-8703(98)70080-8.

Botchkareva "MicroRNA/mRNA regulatory networks in the control of skin development and regeneration" Cell Cycle 11:3, 468-474; (Feb. 2012) Landes Bioscience.

Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11 Imaging and Bioengineering, Dec. 17, 2015).

CalXStars Business Accelerator, Inc.—Website—Justia Patents—Mar. 15, 2017—US Patent Application for Stimulator, Pump & Composition Patent Application (Application #20170266371) https://protect-us.mimecast.com/s/tSaBCxkVlwuDr61CvMWbF?domain=patents.justia.com.

Campbell et al. "Electrical stimulation to optimize cardioprotective exosomes from cardiac stem cells" Med Hypotheses. Mar. 2016; 88:6-9. doi: 10.1016/j.mehy.2015.12.022. Epub Jan. 11, 2016.

Carboni Ei Al. "An initial study on the effect of functional electrical stimulation in erectile dysfunction: a randomized controlled trial" IJIR: Your Sexual Medicine Journal (May 2018) 30:97-101.

Cervera "The interplay between genetic and bioelectrical signaling permits a spatial regionalisation of membrane potentials in model multicellular ensembles," Nature, Scientific Reports, Oct. 12, 2016 volume 6, Article No. 35201 (2016).

Chaikin et al. "Microcurrent stimulation in the treatment of dry and wet macular degeneration" Clinical Ophthalmology 2015:9 2345-2353 (Dec. 2015).

Chen et al. "Beyond anti-VEGF: dual-targeting antiangiogenic and antiproliferative therapy" Am J Transl Res. 2013;5(4):393-403 Published May 24, 2013.

Chen et al. "Nanosecond Pulsed Electric Field (nsPEF) Ablation as an Alternative or Adjunct to Surgery for Treatment of Cancer" Chen et al., Surgery Curr Res 2013, S12 DOI: 10.4172/2161-1076.S12-005.

Choi et al. "Exosomes from human adipose-derived stem cells promote proliferation and migration of skin fibroblasts" Experimental Dermatology. (Sep. 2017) 1-3.

(56) References Cited

OTHER PUBLICATIONS

Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.
Corrigan et al. "Neurogenic inflammation after traumatic brain injury and its potentiation of classical inflammation", Journal of Neuroinflammation, 2016, 13:264; doi://doi.org/10.1186/s12974-016-0738-9.
Costa et al. "Selecting patients for cytotoxic therapies in gastroenteropancreatic neuroendocrine tumours" Best Pract Res Clin Gastroenterol. Dec. 2012;26(6):843-54. doi: 10.1016/j.bpg.2012.12.001. PMID: 23582923.
Costa et al. "Treatment of advanced hepatocellular carcinoma with very low levels of amplitude-modulated electromagnetic fields" Br J Cancer. Aug. 23, 2011;105(5):640-8. doi: 10.1038/bjc.2011.292. Epub Aug. 9, 2011. PMID: 21829195; PMCID: PMC3188936.
Cross Ei Al. "Milk Ejection following Electrical Stimulation of the Pituitary Stalk in Rabbits," Nature 166, 994-995 (Dec. 9, 1950); doi:10.1038/166994b0 (Abstract Only).
Dai Ei Al. "Nanosecond Pulsed Electric Fields Enhance the Antitumour Effects of the mTOR Inhibitor Everolimus against Melanoma," Scientific Reports vol. 7, Article No. 39597 (2017).
Desai et al. "Use of Platelet-Rich Fibrin over Skin Wounds: Modified Secondary Intention Healing" Modified secondary intention healing J Cutan Aesthet Surg (Jan.-Mar. 2013) vol. 6, pp. 35-37.
Deswal Ei Al. "Cytokines and Cytokine Receptors in Advanced Heart Failure An Analysis of the Cytokine Database from the Vesnarinone Trial (VEST)," Circulation. 2001 ;103:2055-2059;://doi.org/10.1161/01. CIR.103.16.2055.
Dimensija "PRF Injections Forprf Forskin Rejuvenationskin Rejuvenationand Tissueand Tissueregenerationregeneration" accessed Aug. 4, 2021, https://dimensija.lv/news/prf-injekcijas-adas-atjaunosanai-un-audu-regeneracijai?lang=en.
Duscher et al. "Stem Cells in Wound Healing: The Future of Regenerative Medicine? A Mini-Review" (May 2015) Stem Cells in Wound Healing, Gerontology 2016;62:216-225.
Fallon "The obvious next step in the evolution of natural rejuvenation" Article (Aug. 2017) (accessed Aug. 4, 2021) https://www.newbeauty.com/platelet-rich-fibrin-skin-rejuvenation-prf/.
FDA "Same Surgical Procedure Exception under 21 CFR 1271.15(b): Questions and Answers Regarding the Scope of the Exception-Guidance for Industry" U.S. Department of Health and Human Services, Food and Drug Administration, Center for Biologies Evaluation and Research, Nov. 2017.
Ferrucci, D. A. "Introduction to This is Watson'," in IBM Journal of Research and Development, vol. 56, No. 3.4, pp. 1:1-1:15, May-Jun. 2012. DOI: 10.1147/JRD.2012.2184356.
Fujiya et al. "Microcurrent Electrical Neuromuscular Stimulation Facilitates Regeneration of Injured Skeletal Muscle in Mice" Journal of Sports Science and Medicine (Jun. 2015) 14, 297-303.
Gavira et al. "Repealed implantation of skeletal myoblast in a swine model of chronic myocardial infarction," Eur. Heart J., 31(8): 1013-1021. doi: 10.1093/eurheartj/ehp342 (2010).
Ge et al. "The aging skin microenvironment dictates stem cell behavior" PNAS (Mar. 2020), vol. 117, No. 10, pp. 5339-5350.
Goldberg et al. "Skin Rejuvenation with Non-Invasive Pulsed Electric Fields" Sci Rep 5, 10187 (May 2015).
Gullestad et al. "Inflammatory cytokines in heart failure: mediators and markers," Cardiology. 2012;122(1):23-35. doi: 10.1159/000338166. Epub Jun. 12, 2012.
Hamzelou et al. "Cancer reversed in frogs by hacking cells' electricity with light," New Scientist This Week, Mar. 16, 2016.
Horsburgh et al. "MicroRNAs in the skin; role in development, homeostasis, and regeneration" Clin Sci (Lond) (Jul.-Aug. 2017) 131 (15): 1923-1940.
Hu et al. "Exosomes derived from human adipose mesenchymal stem cells accelerates cutaneous wound healing via optimizing the characteristics of fibroblasts", Nature Scientific Reports, vol. 6, Article No. 32993 (2016).
Hunckler et al. "A current affair: electrotherapy in wound healing" Journal of Multidisciplinary Healthcare (Apr. 2017)10 179-194.
International Search Report for International Application No. PCT/US2019/025177, dated Sep. 3, 2019, 3 pages.
International Written Opinion for International Application No. PCT/US2019/025177, dated Sep. 3, 2019, 5 pages.
Itatani et al. "Resistance to Anti-Angiogenic Therapy in Cancer-Alterations to Anti-VEGF Pathway" Int J Mol Sci. Apr. 18, 2018;19(4):1232. doi: 10.3390/ijms19041232. PMID: 29670046; PMCID: PMC5979390.
Ivanyi "How Microcurrent Treatments Improve Acne" Envision Acne & Skin Care Center, website accessed Aug. 4, 2021, https://envisionacnecenter.com/microcurrent-treatments-improve-acne/.
Jamal et al. "Klotho, Hypertension and Arterial Stiffness: A Review" Austin J Nephrol Hypertens.(Jul. 2019) 6(2): 1082.
Signature Orthodontics "Accelerated Tooth Movement", http://www.sigortho.com/accelerated-tooth-movement, visited Mar. 15, 2017.
Sisay et al. "The RANK/RANKL/OPG system in tumorigenesis and metastasis of cancer stem cell: potential targets for anticancer therapy" Onco Targets Ther. 2017; 10: 3801-3810.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative *Staphylococci* on Activities of Various Antimicrobial Agents," Antimicrobial Agents and Chemotherapy, vol. 42, (Apr. 1998), pp. 939-941.
Spadari et al., Electrical stimulation enhances tissue reorganization during orthodontic tooth movement in rats; Clinical Oral Investigations, Jan. 2017, vol. 21, Issue 1, pp. 111-120, Abstract.
Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.
Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.
Stenn et al., "Bioengineering the Hair Follicle," Organogenesis, 3(1): 6-13 (Jan.-Mar. 2007).
Stewart et al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.
Stoodley et al., "Influence of Electric Fields and pH on Biofilm Structure as Related to the Bioelectric Effect," Antimicrobial Agents and Chemotherapy, vol. 41, (1997), pp. 1876-1879.
Sultana et al., "Electrochemical Biofilm Control: A Review," Biofouling, vol. 31, (2015), pp. 745-758.
Szkotak et al., "Differential Gene Expression to Investigate the Effects of Low-Level Electrochemical Currents on Bacillus subtilis," AMB Express, vol. 1, (Nov. 2011), 12 pages.
Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009 07.115. Epub Jul. 28, 2009.
Tamaki et al., "Cardiomyocyte Formation by Skeletal Muscle-Derived Multi-Myogenic Stem Cells after Transplantation into Infarcted Myocardium", PLoS One 3(3): e1789. doi: 10.1371/journal.pone.0001789 (Mar. 2008).
Tan et al. "Bioelectric Perturbations in Orthodontic tooth movement" 2010 Journal of Dental Sciences & Research 1:1: pp. 41-49.
Tan et al., "Acupuncture Therapy for Essential Hypertension: a Network Meta-Analysis," Annals of Translational Medicine, vol. 7, (2019), pp. 1-12.
Tavlasoglu et al. "Is partial decalcification of posterior mitral annular bed logical in all mitral valve replacement procedures?" European Journal of Cardio-Thoracic Surgery 43 (2013) 449-450.
Thattaliyath et al., "Modified Skeletal Myoblast Therapy For Cardiac Failure Using AAV SDF1", Proc. Inti. Soc. Mag. Reson. Med. 16, p. 579 (2008).

(56) References Cited

OTHER PUBLICATIONS

Tokyo Medical and Dental University "RANKL expressed by osteocytes has an important role in orthodontic tooth movement" Science Daily Oct. 20, 2017.
Totsugawa, et al. "Ultrasonic annular debridement in minimally invasive aortic valve replacement" Gen Thorac Cardiovasc Surg. Jan. 2020;68(1):81-83 doi: 10.1007/s11748-019-01158-8 Epub Jun. 1, 2019 (Abstract Only).
Trafton, Anne, "A Noninvasive Method for Deep Brain Stimulation," MIT News Office, (available at http://news.mit.edu/2017/noninvasive-method-deep-brain-stimulation-0601), (Jun. 1, 2017), 3 pages.
Ucirvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.
Valvublator Heart Valve Regeneration, accessed Apr. 24, 2020 https://valvublator.com (6 pages).
Van Dam et al. "RANK/RANKL signaling inhibition may improve the effectiveness of checkpoint blockade in cancer treatment" Critical Reviews in Oncology/Hematology vol. 133, Jan. 2019, pp. 85-91.
Verna et al. "The rate and the type of orthodontic tooth movement is influenced by bone turnover in a rat model" European Journal of Orthodontics 22 (2000) 343-352.
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Vinod Krishnan, Ze'ev Davidovitch (eds.), Biological Mechanisms of Tooth Movement, (John Wiley & Sons 2015 (10 Pages).
Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.
Walsh & Choi "Biology of the RANK* RAN* OPG System in Immunity, Bone, and Beyond", Front Immunol. 2014; 5: 511.
Wang et al., "Controlling *Streptococcus mutans* and *Staphylococcus aureus* Biofilms With Direct Current and Chlorhexidine," AMB Express, vol. 7, (Nov. 2017), 9 pages.
Warner"Inflammation Adds to Blood Pressure Risks, High Blood Pressure and C-Reactive Protein May Trigger Heart Attack, Stroke" Art. WebMD Health News (2003) 2 pages.
Wei et al., "Epicardial FSTL1 reconstitution regenerates the adult mammalian heart," Nature 525: 479-485 (Sep. 24, 2015).
Welch "RGS2 Proteins Regulate Blood Pressure" JASN Nov. 2010, 21 (11) 1809-1810.
Wellman et al., "Bacterial Biofilms and the Bioelectric Effect," Antimicrobial Agents and Chemotherapy, vol. 40, (1996), pp. 2012-2014.
What Is Elastin? http://www.keracyte.com/index.php/site/page?view=whatIsElastin, Mar. 1, 2017.
Wong et al., "Dual Functional Polyelectrolyte Multilayer Coatings for Implants: Permanent Microbicidal Base With Controlled Release of Therapeutic Agents," Journal of the American Chemical Society, vol. 132, (2010), pp. 17840-17848.
Wu et al., "Vascular Calcification: an Update on Mechanisms and Challenges in Treatment," Calcified Tissue International, vol. 93, (Oct. 2013), pp. 365-373.
Yamaguchi, "RANK/RANKL/OPG during orthodontic tooth movement", Orthod Craniofac Res. May 2009; 12(2):113-9. doi: 10.1111/j.1601-6343.2009.01444.x.
Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4 (3):312-5 (Dec. 1999).
Yang "Effect RANKL Produced by Periodontal Ligament Cells on Orthodontic Tooth Movement" (2016) Dental Theses. Paper 13.

Yang et al., "Acupuncture for hypertension," Cochrane Database of Systematic Reviews, Available Online at < https://www.cochranelibrary.com/cdsr/doi/10.1002/14651858.CD008821.pub2/full >, (2018), 4 pages.
Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.
Yarbrough et al., "Specific Binding and Mineralization of Calcified Surfaces by Small Peptides," Calcified Tissue International, vol. 86, (2010), pp. 58-66.
Yu et al. "Association between inflammation and systolic blood pressure in RA compared to patients without RA" Arthritis Research & Therapy vol. 20, Article No. 107 (2018).
Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.
Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.
Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).
Zhang et al. "Exosomes derived from human embryonic mesenchymal stem cells promote osteochondral regeneration", Osteoarthritis and Cartilage, vol. 24, Issue 12, Dec. 2016, pp. 2135-2140.
Zhang et al., "Comparison of arterial slirtness in non-hypertensive and hypertensive population of various age groups," Jan. 24, 2018, 2 pages (Abstract Only).
Zhang et al., "Highly Stable and Reusable Imprinted Artificial Antibody Used for in Situ Detection and Disinfection of Pathogens," Chemical Science, vol. 6, (2015), pp. 2822-2826.
Leonhardt "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.
Leonhardt, H.—Leonhardt Announces Vibrational Energy Device For Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.
Li "Regulation of Renal Oxygenation and Blood Pressure" Art. Virginia Commonwealth University, Richmond, VA, United States (Abstract), Mar. 1, 2019.
Li et al., "Exogenous IGF-1 promotes hair growth by stimulating cell proliferation and down regulating TGF-(Beta)1 in C57BL/6 mice in vivo" Growth Hormone & IGF Research, vol. 24, Issues 2-3, pp. 89-94 (Apr.-Jun. 2014).
Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Li et al., "The Mechanism of Acupuncture in Treating Essential Hypertension: A Narrative Review," International Journal of Hypertension, vol. 2019, (2019), Article ID 8676490, 10 pages.
Li, et al. "Local injection of RANKL facilitates tooth movement and alveolar bone remodelling." Oral Diseases, 25(2), 550-560. https://doi.org/10.1111/odi.13013, Dec. 7, 2018.
Liang et al. "Therapeutic effect of low-intensity pulsed ultrasound on temporomandibular joint injury induced by chronic sleep deprivation in rats" Am J Transl Res. 2019; 11(6): 3328-3340.
Longhurst et al. "Evidence-based blood pressure reducing actions of electroacupuncture: mechanisms and clinical application" Sheng Li Xue Bao. Oct. 25, 2017; 69(5): 587-597.

\* cited by examiner

US 11,691,007 B2

BIOELECTRIC OPG TREATMENT OF CANCER

CROSS-REFERENCE TO RELATED APPLICATIONS

This application is a continuation-in-part of U.S. patent application Ser. No. 16/137,035, filed on Sep. 20, 2018 (US 20190030330 (Jan. 31, 2019)), which is a continuation-in-part of U.S. patent application Ser. No. 15/460,129, filed on Mar. 15, 2017 (U.S. 2017/0266371A1, Sep. 21, 2017), which itself claims the benefit under 35 USC § 119 of U.S. Provisional Patent Application Ser. No. 62/308,702, filed Mar. 15, 2016, U.S. Provisional Patent Application Ser. No. 62/363,012, filed Jul. 15, 2016, U.S. Provisional Patent Application Ser. No. 62/364,472, filed Jul. 20, 2016, U.S. Provisional Patent Application Ser. No. 62/375,271, filed Aug. 15, 2016, U.S. Provisional Patent Application Ser. No. 62/385,124, filed Sep. 8, 2016, U.S. Provisional Patent Application Ser. No. 62/454,521, filed Feb. 3, 2017, and U.S. Provisional Patent Application Ser. No. 62/352,930, filed Jun. 21, 2016, the disclosure of each of which is incorporated herein in its entirety by this reference.

This application is also a continuation-in-part of application Ser. No. 15/812,760, filed Nov. 14, 2017 (US 2018/0064935 A1, Mar. 8, 2018), which is a continuation-in-part of U.S. Ser. No. 15/460,129, filed on Mar. 15, 2017 (US 2017/0266371A1, Sep. 21, 2017), which itself claims the benefit under 35 USC § 119 of U.S. Provisional Patent Application Ser. No. 62/308,702, filed Mar. 15, 2016, U.S. Provisional Patent Application Ser. No. 62/363,012, filed Jul. 15, 2016, U.S. Provisional Patent Application Ser. No. 62/364,472, filed Jul. 20, 2016, U.S. Provisional Patent Application Ser. No. 62/375,271, filed Aug. 15, 2016, U.S. Provisional Patent Application Ser. No. 62/385,124, filed Sep. 8, 2016, U.S. Provisional Patent Application Ser. No. 62/454,521, filed Feb. 3, 2017, and U.S. Provisional Patent Application Ser. No. 62/352,930, filed Jun. 21, 2016, the disclosure of each of which is incorporated herein in its entirety by this reference.

This application is also a continuation in part of U.S. application Ser. No. 15/471,954, filed Mar. 28, 2017, which claims the benefit under 35 USC § 119 of U.S. Provisional Patent Application Ser. No. 62/314,240, filed Mar. 28, 2016, the disclosure of each which is incorporated herein in its entirety by this reference.

TECHNICAL FIELD

The application relates generally to the field of medical devices and associated treatments, and to precise bioelectrical stimulation of a subject's tissue, potentially augmented with the administration of a composition comprising, among other things, stem cells and nutrients, useful to stimulate and treat the subject, the subject's tissue(s), the subject's organ(s), and/or the subject's cells. More specifically described is a bioelectric therapy protocol for cancer, especially, multiple myeloma or bone cancer treatment.

BACKGROUND

Multiple myeloma is a cancer in which plasma cells grow out of control. Healthy plasma cells come from bone marrow and play an important role in the immune system. With multiple myeloma however, the plasma cells create a buildup of an abnormal protein in bones and blood, which can lead to symptoms such as bone pain, anemia, and infections. Multiple myeloma is rarely cured, so treatments typically focus on relieving symptoms, reaching remission, and helping the patient live longer. Existing treatments include targeted therapies and stem cell transplants.

As described by S. Goranov (2004) infra, multiple myeloma induces considerable imbalance in the osteoprotegerin ("OPG"), receptor activator of nuclear factor KB ligand ("RANKL") and RANK system. Signaling pathways for differentiation and proliferation of an osteoclastic line activates RANKL's binding to RANK on the surface of osteoclastic precursors in the presence of m-CSF. OPG is a decoy circulating receptor for RANKL that blocks RANKL's binding to RANK. At least three mechanisms exist by which myeloma cells affect the RANK/RANKL/OPG system. First, the adhesion between myeloma/stromal cells and the osteoblastic precursors stimulates the system by increasing the production of RANKL. Second, some myeloma lines produce membrane-bound or free RANKL. Third, the normal and mutated plasma cells bind, degrade, and block OPG production from stromal cells. The first results from the application of a synthetic analogue of OPG, as well as by RANKL antagonists or RANK inhibitors, which show decrease in the number of osteoclasts, osteolytic lesions, and M-gradient.

A number of published studies have linked a role of RANK/RANKL signaling in patients with multiple myeloma, who have increased serum levels of soluble RANKL and an imbalance in RANKL and OPG. Current therapies for patients with multiple myeloma demonstrate that RANKL may be released by tumor cells or OPG osteoprogenitor cells. This RANKL overexpression in simple terms eats away and destroys bone in multiple myeloma patients.

Previous research has focused on injecting or infusing OPG for inhibiting RANKL over expression and thus reducing or stopping bone degradation.

BRIEF SUMMARY

Described is the application of a bioelectric signals or signals to upregulate expression of OPG at levels in a multiple myeloma patient that inhibit over-expression of RANKL and thus also inhibit bone degradation in the multiple myeloma patient. This treatment may be combined with other bioelectric signal treatment protocols (such as those described in the incorporated U.S. 2018/0064935 A1) in an attempt to control cancer spread in the patient.

Disclosed are means for upregulating the expression of OPG to inhibit RANKL over-expression in a subject. Typically, the subject will have been diagnosed with cancer, breast cancer, bone cancer, lung cancer, osteoporosis, multiple myeloma, and a combination of any thereof. Bioelectric signaling is utilized to deliver an effective and safe option for patients with fewer toxic side effects than may be experienced with chemo and radiation therapies.

RANKL and its decoy receptor OPG are regulators of bone homeostasis and have been implicated in the development and progression of, for example, breast cancer. Rachner et al. (2019) infra demonstrated that high levels of OPG were an independent prognostic marker for breast cancer-specific survival ("BCSS"), while relatively high levels of RANKL indicated improved BCSS in disseminated tumor cell ("DTC")-negative patients. RANKL levels were increased in DTC-positive patients and in patients who later developed bone metastases.

The described bioelectric signaling technology targets specific cancers such as multiple myeloma. The technology is based on bioelectric controlled expression of OPG to inhibit RANKL over production, which otherwise eats away at bone in multiple myeloma patients and contributes to the spread of other cancers such as lung cancer(s).

Described is a bioelectric stimulator programmed to produce a bioelectric signal or bioelectric signals that stimulate(s) target tissue in a subject, wherein the bioelectric signal(s) comprise(s) a signal of, within 15%, 4.0 milliVolt (mV), 2,000 Hz, square wave, and/or a signal of from 3 mV to 5 mV at a frequency range of 1 to 3 MHz, and a duration range of 30 to 40 mW/cm$^2$ for a minimum of 20 to 45 minutes. Such bioelectric signals, applied to a human cell or tissue, increase the expression of OPG by the cell or tissue.

In certain embodiments, the bioelectric stimulator of claim 1, wherein the bioelectric stimulator is further programmed to produce a signal of 3.0 mV, 2 Hz, square wave; 3 mV at 2/100 Hz alternating frequency with current of 3 mA followed by 15 Hz, 1 Gauss EM field, consisting of 5-millisecond bursts with 5-microsecond pulses followed by 200-µs pulse duration at 30 Hz and with current amplitude of 140 mA; and/or a biphasic pulse at 20 Hz, 0.1 V, and a 7.8 ms pulse duration. Such bioelectric signals, applied to a human cell or tissue, increase the expression of RANKL by the cell or tissue. Such expression can be used to offset OPG expression if needed.

Such a bioelectric stimulator may be used to treat a subject diagnosed as suffering from, e.g., a disorder selected from the group consisting of cancer, breast cancer, bone cancer, lung cancer, osteoporosis, and a combination of any thereof, by delivering the bioelectric signal(s) to tissue of the subject. Particularly, a subject suffering who has been diagnosed with multiple myeloma may be treated with the thus programmed bioelectric stimulator.

In certain embodiments, the method of treatment further includes separately delivering to the subject an admixture comprising any combination of the following: stem cells, endothelial progenitor cells, selected exosomes, selected alkaloids, selected anti-inflammatory agents, nutrient hydrogel, organ-specific matrix, selected growth factors, amniotic fluid, placenta fluid, cord blood, and embryonic sourced growth factors and cells.

A system that utilizes the method typically includes:

1. A bioelectric stimulator programmed as described.
2. A micro infusion pump (e.g., a FluidSync™ micropump available from Fluidsynchrony of Pasadena, Calif., US), which is programmable and re-fillable and preferably has a low cell damage design. Such a pump preferably includes a refilling silicon septum port or ports and reservoir chambers.
3. A multi-component organ regeneration composition that includes (depending on the application) adipose-derived stem cells, muscle-derived stem cells (when needed for muscle), exosomes, Micro RNAs, nutrient hydrogel, growth factor cocktail, organ-specific matrix, selected alkaloids, and/or selected anti-inflammatory agents.

The pump and stimulator may be associated with (e.g., connected to) the organ to be treated/regenerated with a pacing infusion lead (available from Nanoscribe of Eggenstein-Leopoldshafen, Germany). The interface with the organ varies by organ, e.g., a conductive soft wrap can be used for certain applications.

Typical treatment times for the OPG bioelectric signals are 20 minutes 2 or 3 times a week (e.g. applied to the patient's jaw). Brain electrodes may also be used to apply the signal. In certain embodiments, the patient is stimulated eight times per day with the OPG bioelectric signal until RANKL is determined to be in balance (which may be determined via an analysis of a blood sample.)

Treatment tissues include the jaw, thigh, leg(s), hip, front, and back, or, in certain circumstances, electrode into the bone marrow, which electrode is connected to an implantable stimulator.

DETAILED DESCRIPTION

In the incorporated US 20190030330, described is, among other things, a multi-modality bioelectric cancer treatment protocol involving certain novel bioelectric signaling sequences for controlling specific actions, which may be adapted to the instant application. The described treatment is customized based on reading the cancer tumors real time with specific signaling sequences delivered customized based on that read. The first wave of bioelectric signals sent to the tumors are designed to jam their communication. The second set of signals are designed to change the surface proteins and electrical surface charge of the tumors to elicit an immune response from the body to kill off the tumor. These signals are specifically designed to elicit a T cell response targeting the proliferating cancer cells. The third wave of treatment is designed to starve a tumor of blood supply by controlled release of anti-angiogenic proteins. The fourth wave of signaling targets the re-programming of cancer cells to re-direct their tumor development pathway. After all of these treatments phases are completed, the bioelectric signaling sequences transition to a promotion of healing and regeneration of the diseased organ including bioelectric inflammation management.

Bioelectric signals may be combined with protein expression and/or release signals, which can be used to, e.g., cut off the blood supply to the cancer tumor. For example, bioelectric signaling can lead to preferably the enhanced expression and/or release of thirteen or more selected proteins (e.g., ones useful for organ regeneration, stopping cell division, enhancing the patient's immunological response, and inhibiting blood supply to the cancer tumor and surrounding tissues). (See, e.g., the bioelectric signals and proteins described in the incorporated US 2018/0064935 A1)

Figure 1:
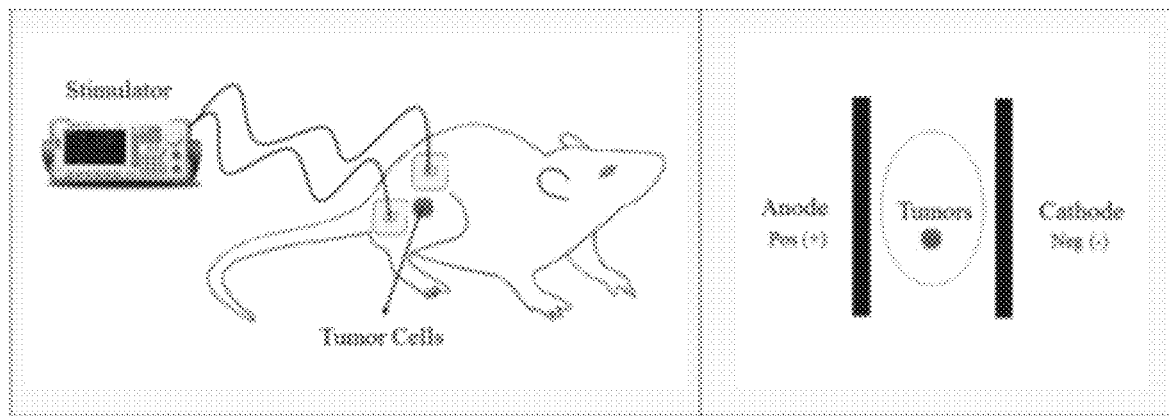
FIG. 1 depicts a programmed bioelectric stimulator for delivery to cells of a subject via two electrodes. The anode wire/electrode may be placed directly into a tumor or adjacent to the tumor.
Figure 2:
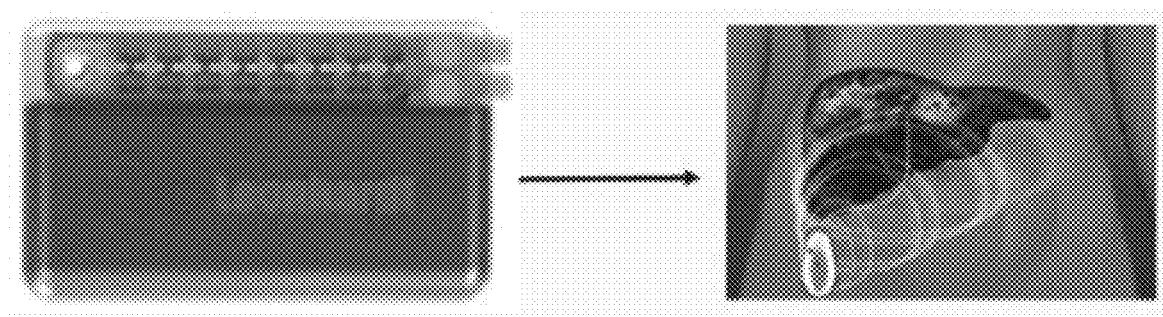
FIG. 2 depicts an implantable lead with simulated therapy for liver cancer.

Referring to FIG. 1, depicted is a stimulator for use with treatment of, e.g., a cancer tumor. Preferably, such a device is about the size of two quarters (FIG. 2).

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBALeonhardt's Launchpads or Leonhardt Vineyards LLC DBA Leonhardt Ventures of Salt Lake City, Utah, US). The primary difference is the special electrical stimulation signals needed to control, e.g., precise OPG release on demand (which signals are described herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

Micro stimulators may be purchased or constructed in the same manner heart pacemakers have been made since the 1960's. Micro infusion pumps can be purchased or produced similar to how they have been produced for drug, insulin, and pain medication delivery since the 1970's. The programming computer can be standard laptop computer.

The programming wand customary to wireless programming wands may be used to program heart pacers. A re-charging wand for use herein is preferably similar to the pacemaker re-charging wand developed by Alfred Mann in the early 1970's for recharging externally implantable pacemakers.

Bioelectric stimulation can be done with the described microstimulator, which has a pacing infusion lead with a corkscrew lead placed/attached. The microstimulator is actuated and runs through programmed signals to signal the release of, e.g., OPG. Up-regulation of RANKL and osteoprotegerin ("OPG") was achieved in bone, tooth, and gum.

In certain embodiments, a signal generator coupled with a voltage amplifier is set to apply electrical stimulation as described herein via needle electrode pair to tumors.

A pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

Wireless, single lumen infusion pacing lead(s) or infusion conduction wide array patch(es) may all be used to deliver the regeneration signals and substances to the organ of interest to be treated or they may be used in combination.

An infusion and electrode wide area patch may be constructed by cutting conduction polymer to shape and forming plastic into a flat bag with outlet ports in strategic locations.

Figure 4:
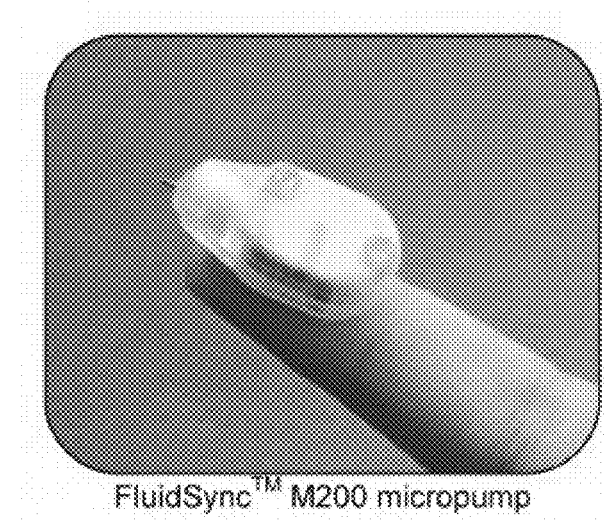
FIG. 4 depicts a micropump for use with the system.

The healing process can be accelerated with the use of a micro infusion pump that is filled with various types of stem cells and growth factors and in some cases drugs. Thus, in certain embodiments, the system includes a microinfusion pump (FIG. 4) for continuous or repeat delivery of a liquid composition, which microinfusion pump includes silicon septum ports and associated reservoir chambers connected to the bioelectric stimulator microinfusion pump to the tissue with a pacing infusion lead. The pump is preferably programmable and re-fillable with low cell damage design. Refilling may be by silicon septum ports and reservoir chambers.

In certain embodiments, the system includes an organ regeneration composition comprising, for example, adipose-derived stem cells, bone marrow-derived stem cells, muscle-derived stem cells (e.g., when needed for muscle), exosomes, MicroRNAs, nutrient hydrogel, growth factor cocktail, organ-specific matrix, selected alkaloids, and/or selected anti-inflammatory agents.

An organ-specific matrix is a composition comprising cells of an organ which is to be treated. The organ-specific matrix is believed to aid in stem cell differentiation, but in any event is found to be useful in the composition. It has been found that for the multicomponent composition, cells plus selected growth factors are better than just cells alone. See, e.g., Procházka et al. "Therapeutic Potential of Adipose-Derived Therapeutic Factor Concentrate for Treating Critical Limb Ischemia," *Cell Transplantation*, 25(9), pp. 1623-1633(11) (2016) and "Cocktail of Factors from Fat-derived Stem Cells Shows Promise for Critical Limb Ischemia," world wide web at sciencenewsline.com/news/2016012204520017.html (Jan. 22, 2016), the contents of each of which are incorporated herein by this reference.

Figure 3:
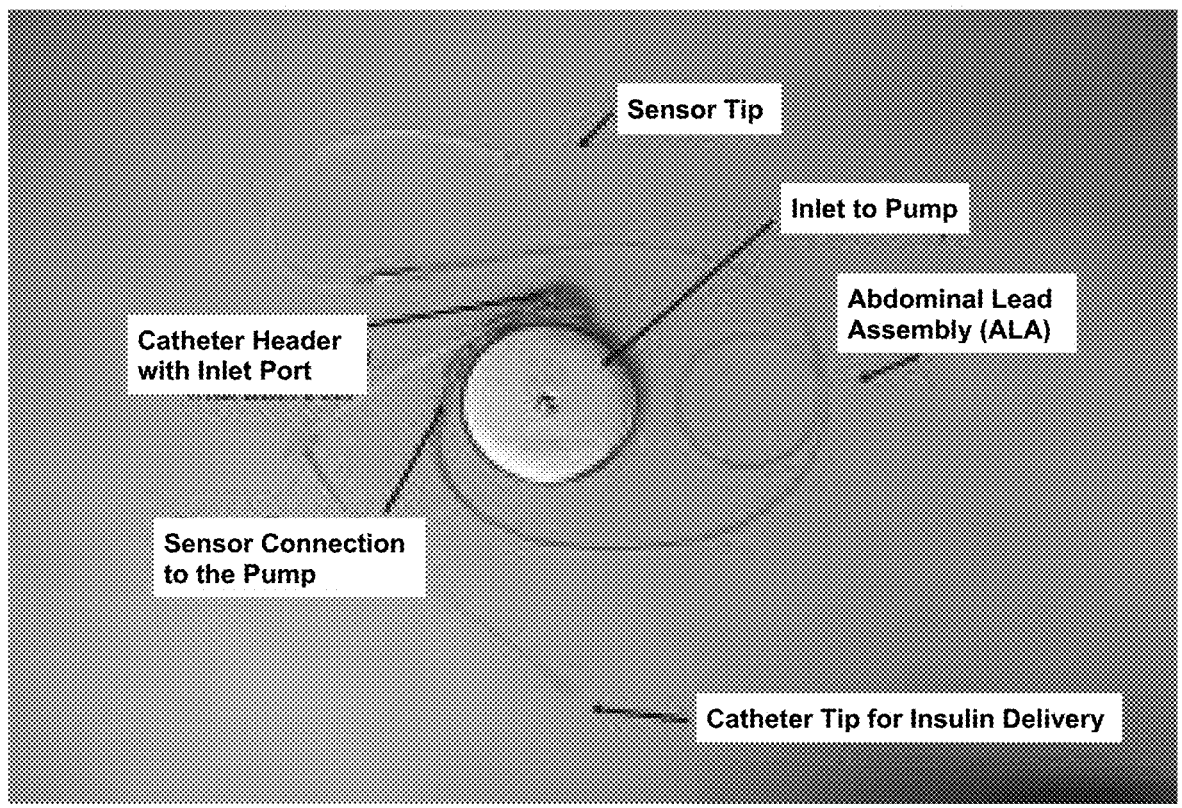
FIG. 3 depicts an interface for use with the system.

In case of an advanced disease state, a micro infusion pump (e.g., FIGS. 3 and 4) may be used for daily delivery of, e.g., 2 ml of organ regeneration composition (comprised of adipose-derived cells or bone marrow-derived mesenchymal stem cells plus cocktail of growth factors (usually derived from amniotic fluid or placenta), selected Micro RNAs, selected alkaloids, selected anti-inflammatory agents, nutrient hydrogel, organ-specific matrix, selected exosomes). For muscle regeneration, immature myoblasts are included in the composition.

Exosomes represent a specific subset of secreted membrane vesicles, which are relatively homogeneous in size (30-100 nm). Exosomes have been proposed to differ from other membrane vesicles by its size, density, and specific composition of lipids, proteins, and nucleic acids, which reflect its endocytic origin. See Campbell et al. "Electrical stimulation to optimize cardioprotective exosomes from cardiac stem cells" *Med Hypotheses*. 2016 March; 88:6-9. doi: 10.1016/j.mehy.2015.12.022. Epub 2016 Jan. 11.

One such composition includes adipose-derived cells (or bone marrow derived MSCs or any pluripotent stem cell, such as iPS cells) and growth factor mix which should include (SDF-1, IGF-1, EGF, HGF, PDGF, VEGF, eNOS, activin A, activin B, follistatin, relaxin, GDF-10, GDF-11 and tropoelastin plus selected exosomes (miR-146a, miR-294, mES-Exo) plus selected alkaloids (harmine and tetra-hydroharmine) plus selected anti-inflammatory factors plus nutrient hydrogel (IGF-1, SDF-1, HGF plus FGF) plus organ-specific matrix. Also, preferably included are amniotic fluid, placenta, or cord blood when available.

The concentration of cells in the compositions is preferably about 50,000,000 cells/ml. The amniotic fluid is preferably as described in Pierce et al. "Collection and characterization of amniotic fluid from scheduled C-section deliveries," *Cell Tissue Bank*, DOI 10.1007/s10561-016-9572-7 (Springer, 2012) and is available from Irvine Scientific.

In certain embodiments, a mixed composition is loaded into a micro infusion pump. The pump may be refilled, e.g., weekly to achieve a slow, timed infusion delivery of the composition to the heart scar tissue. Administration of the composition(s) is combined with bioelectric stimulation to control the release of desired proteins. Treatment times for assisting the heart may last 36 months.

Figure 7:
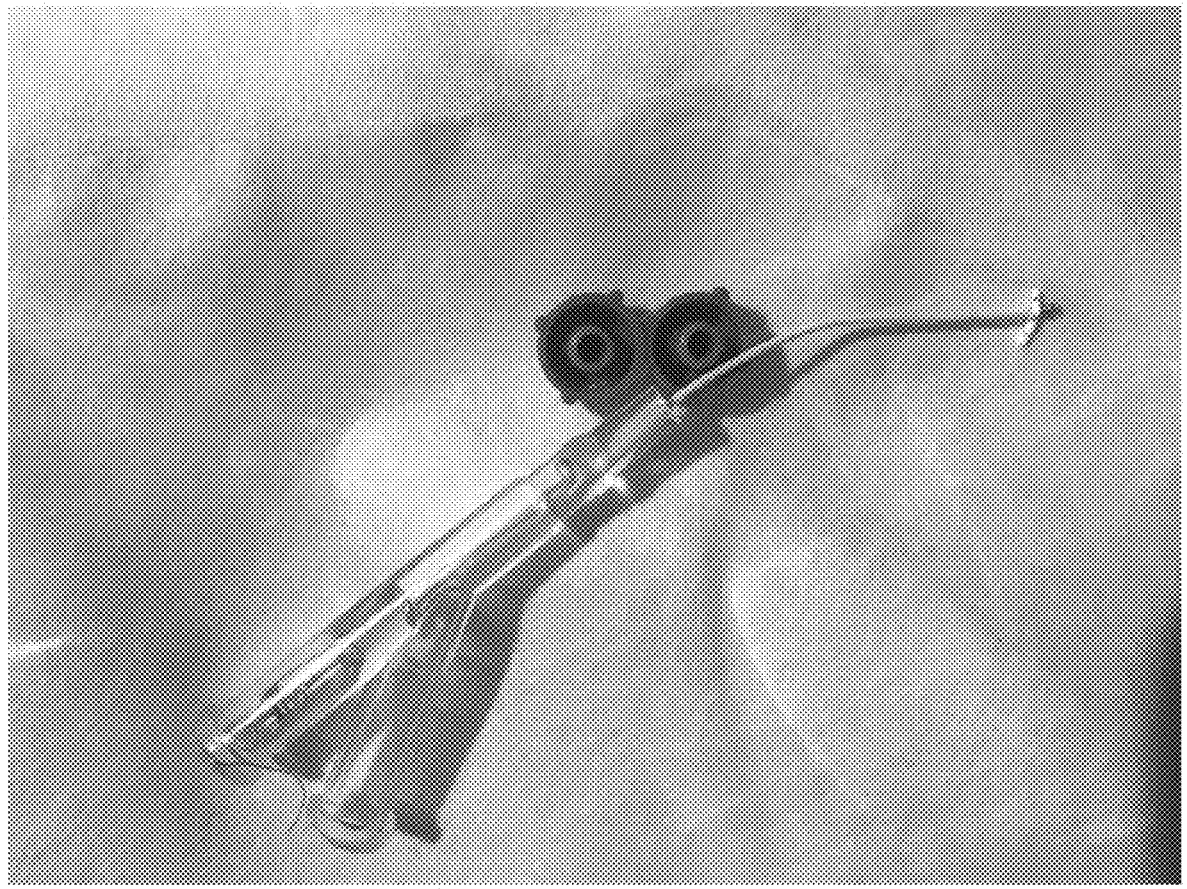
FIG. 7 depicts a combination bioelectric stimulation and stem cells and growth factors infusion catheter.

FIG. 7 depicts a combination bioelectric stimulation and stem cell and growth factor(s) infusion catheter usable with the described system.

Figure 8:
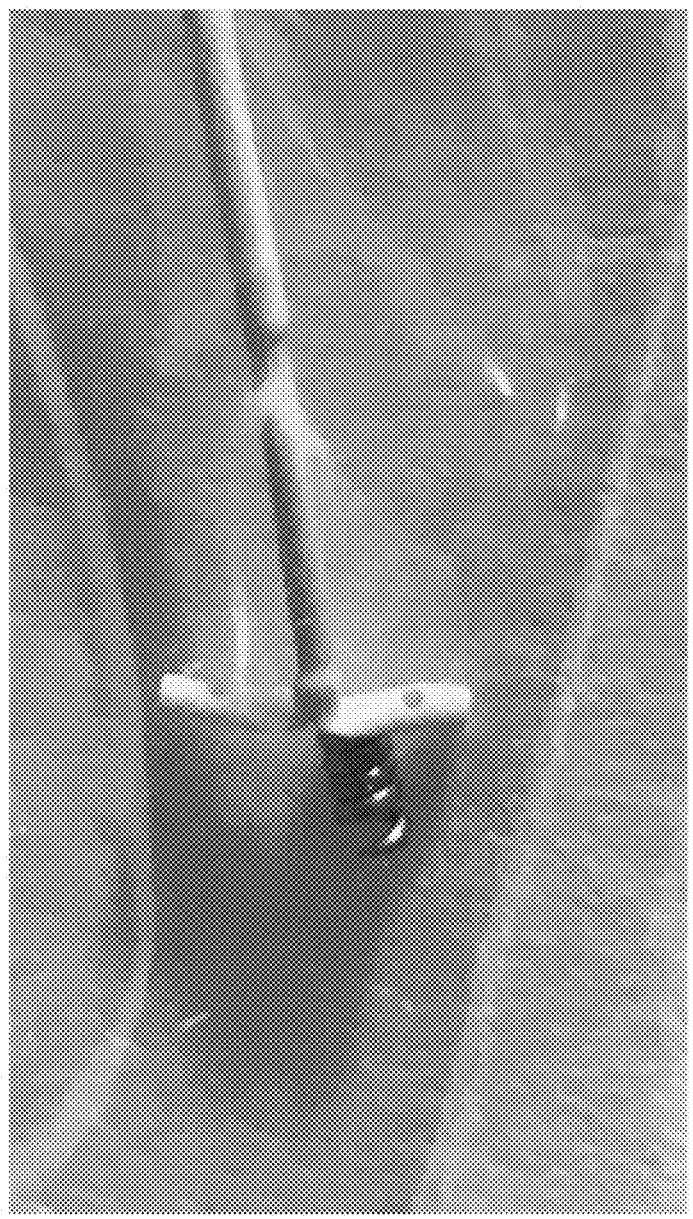
FIG. 8 is a close up view of the conductive and infusion cork screw tip for use with the catheter system of FIG. 7.

A corkscrew tip may be of a standard type utilized to secure most heart pacemakers in heart tissue. Wireless delivery of the signal or electro-acupuncture needle delivery is included. FIG. 8 is a close up of the conductive and infusion cork screw tip for getting deep into target tissue. The tip includes suture tabs for even more secure fixation to the target organ.

Several types of drugs are used to treat multiple myeloma and their respective therapies and dosages are known by those of skill in the art. Such drugs may be taken singly or as a combination. Useful chemotherapeutic agents include bendamustine, cyclophosphamide, doxorubicin, etoposide, liposomal doxorubicin, melphalan, and vincristine. Useful corticosteroids include dexamethasone and prednisone. Useful immunomodulators include lenalidomide, pomalidomide, and thalidomide. Useful monoclonal antibodiesd daratumumab, elotuzumab, and isatuximab. Panobinostat is a useful Histone Deacetylase (HDAC) inhibitor. Useful proteasome inhibitors include bortezomib, carfilzomib, and ixazomib. Selinexor is a useful nuclear export inhibitor.

When combined with the described OPG bioelectric signal treatment of multiple myeloma, the drug dosage may be less than 20% of a standard dosage for the drug.

A week after treatment, samples can be collected for morphometric evaluation by in-situ hybridization or RT-PCR.

Figure 5:
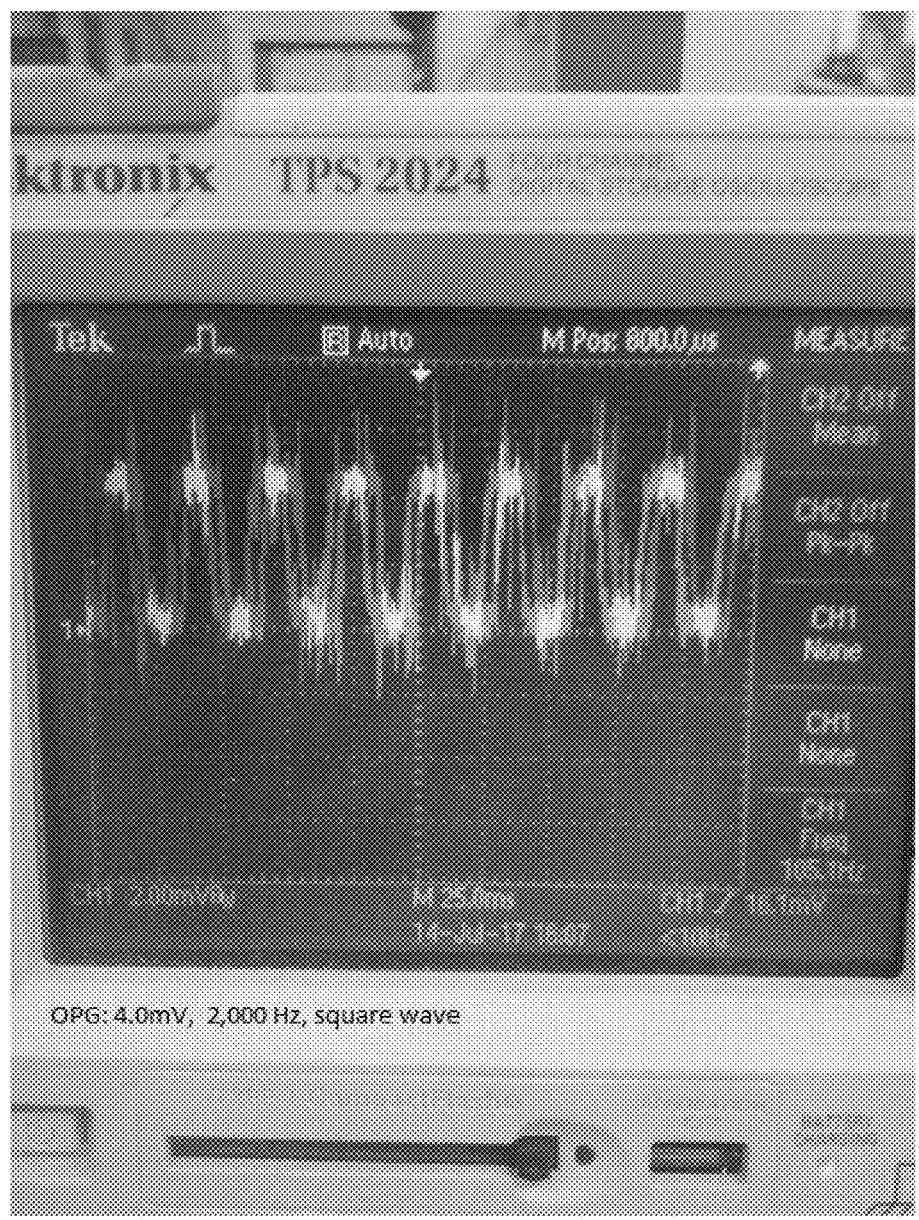
FIG. 5 depicts an image of a signal (voltage and frequency) associated with OPG: 4.0 mV, 2,000 Hz, square wave.
Figure 6:
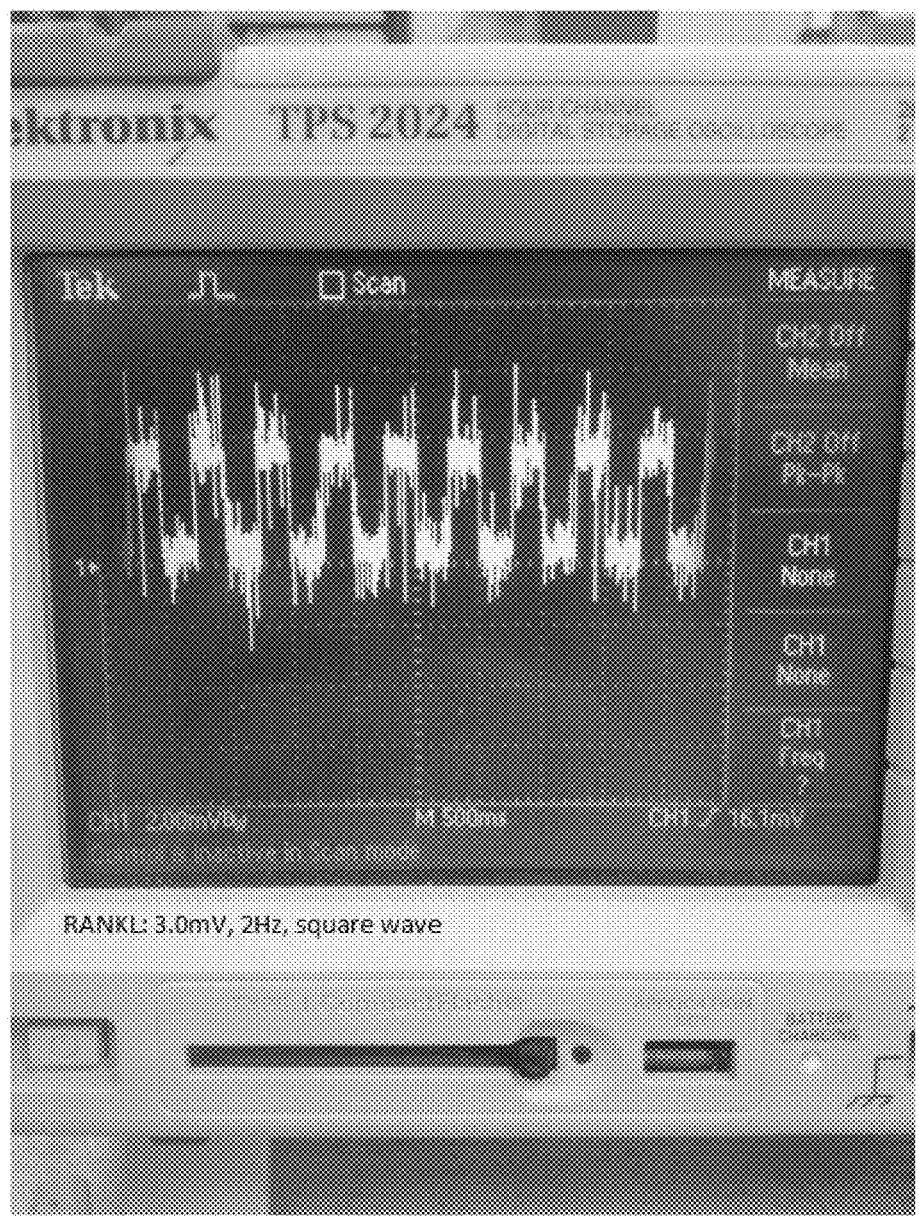
FIG. 6 depicts an image of the signal (voltage and frequency) associated with RANKL: 3.0 mV, 2 Hz, square wave.

FIGS. 5 & 6 are images of signals with the name, voltage, and frequency of each signal written on each image. The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Specifically, FIG. 5 depicts an image of the signal (voltage and frequency) associated with OPG: 4.0 mV, 2,000 Hz, square wave. Applying this bioelectric signal to gingival cells, eye cells, and rat teeth has increased OPG protein levels in the cells up to 2,300%.

FIG. 6 depicts an image of the signal (voltage and frequency) associated with RANKL: 3.0 mV, 2 Hz, square wave.

The invention is further described with the aid of the following illustrative Examples.

Examples

Relationship Between the Components

The micro voltage signal generator is attached to a pacing infusion lead with, e.g., a corkscrew tip or conductive polymer bandage or patch to the tissue or organ to be treated. An external signal programmer may be used to program the micro voltage signal generator with the proper signals for treatment including the follistatin producing signal. The device battery or other power source (not shown) may be re-chargeable with an external battery charging wand.

In use, the signal generator sends a bioelectric signal to the target tissue, which signal causes the tissue to upregulate expression of OPG. The essential elements are the micro voltage signal generator and the means for delivering the signal to the target tissue.

The signal generator may be external or internal. The transmission of the signal may be wireless, via liquid and/or via wires.

The tissue contact interface may be a patch or bandage or may be via electrodes or leads.

A micro infusion pump may be included to the system for delivering other supportive or therapeutic substances.

The described system upregulates expression of OPG under precise dosing control at safe and comfortable low voltages.

The signal generator programmed with the OPG release signal is directed via a lead, bandage of patch to the target organ tissue in need of muscle repair or build up.

Example—Treating Cancer Tumors Using Bioelectric Stimulation in Combination with Micro Infusion Previous cancer treatments failed to address the combination of stopping cell proliferation and blood supply followed by regenerating the damaged tissue or organ.

Cytokine and chemotherapeutic and regenerative treatment for certain cancers may be combined with low intensity, intermediate frequency alternating electric fields that are tuned to release specific beneficial proteins at specific time intervals. More specifically, cell proliferation inhibition and halting blood supply to tumors in the first treatment stage. The bioelectric stimulation treatment may be increased in volume and efficacy by the combination use of an implantable, programmable, re-fillable micro infusion pump that delivers anti-cell proliferation and anti-blood vessel growth proteins as well, if desired, standard cancer treatment drugs such as chemo therapy agents. The second stage of treatment is focused regeneration of cancer damaged tissues back to their most optimal healthy state. The regenerative phase comprises a sequence of recruiting reparative stem cells to the damaged organ by bioelectrically stimulating the release of SDF-1 (stem cell homing factor), followed by a controlled proliferation signal, a controlled blood vessel supply signal (VEGF) and if desired and useful release of Follistatin, tropoelastin, HGF, IGF-1 and Activin. The stimulation cycle causing release of beneficial proteins for regeneration may be upgraded in volume and speed of delivery by the combination use of an implantable, re-fillable, programmable micro infusion pump for delivering a higher quantity of stem cells, nutrient hydrogel, matrix and beneficial tissue and organ regeneration promotion proteins.

Cytokine and Chemotherapeutic and regenerative treatment for certain cancers comprising a combination low intensity, intermediate frequency alternating electric fields that are tuned to release particular beneficial proteins in two stages, stage (1) is stopping cancer spread by halting cell proliferation and halting tumor blood supply and stage (2) regenerating the cancer damaged tissue or organ back to optimal health. In many cases, the resulting cell proliferation inhibition is significantly higher than the inhibition obtained by drug-only regimens of treatment.

A method of killing or inhibiting the growth of cancer cells in a target region followed by regenerating the tissue or organ back to optimal health, the method comprising the steps of:

Stage 1=Stop cancer growth by:

Applying, to the target region, a series of bioelectric signals that damages the cancer cells or inhibits the growth of the cancer cells via stopping cell proliferation and halting blood supply temporarily, but leaves normal cells in the target region substantially unharmed; and Treating the cancer cells with another anti-cancer regimen via programmable micro pump infusion, wherein the applying step and the treating step are performed simultaneously.

Stage 2=Regeneration of post-cancer tissue or organ by:

Treating the target region with a series of bioelectric signals to recruit stem cells, grow healthy blood vessels and re-grow healthy functional tissues in the previous cancer damaged region In such a method, in the applying step, the field may be applied in at least two different directions in an alternating sequence to halt cell proliferation and to stop blood supply to the cancer tumor.

In such a method, the other anti-cancer regimen may comprise treating the cancer cells with an anti-cancer drug. In this method, the drug may comprise at least one drug selected from the group consisting of paclitaxel, doxorubicin cyclophosphamide, and cisplatin. In such a case, the drug dosage may be less than 20% of a standard dosage for the drug.

In such a method, the bioelectric stimulation may release any one of these regeneration of tissue and organ beneficial proteins SDF-1, IGF-1, Activin, HGF, VEGF, Follistatin or tropoelastin and in specific sequences for optimal organ health.

In such a method, all bioelectric regeneration signal may be delivered wirelessly and/or non-invasively.

In such a method, the target cancer may be breast cancer and the target regenerative organ may be breast reconstruction.

REFERENCES (The contents of the entirety of each of which is incorporated herein by this reference.) Ando et al. "RANKL/RANK/OPG: key therapeutic target in bone oncology" *Curr Drug Discov Technol.* 2008 September; 5(3): 263-268.

Bi et al. "Key Triggers of Osteoclast-Related Diseases and Available Strategies for Targeted Therapies: A Review" *Front Med (Lausanne).* 2017; 4: 234. doi: 0.3389/fmed.2017.00234.

Buckle et al. "Soluble Rank Ligand Produced by Myeloma Cells Causes Generalised Bone Loss in Multiple Myeloma" *PLoS One.* 2012; 7(8): e41127. doi: 10.1371/journal.pone.0041127 PMCID: PMC3430669.

Christouls et al. "Pathogenesis and Management of Myeloma Bone Disease" *Expert Rev Hematol.* 2009; 2(4): 385-398.

Fili et al. "Therapeutic implications of osteoprotegerin" *Cancer Cell International* volume 9, Article number: 26 (2009).https://doi.org/10.1186/1475-2867-9-26.

S. Goranov "Bone Lesions in Multiple Myeloma—The OPG/RANK-ligand System" *Folia Med (Plovdiv).* 2004; 46(3): 5-11.

Goswarmi et al. "Osteoprotegerin rich tumor microenvironment: implications in breast cancer" *Oncotarget.* 2016 Jul. 5; 7(27): 42777-42791.

Holen & Shipman "Role of Osteoprotegerin (OPG) in Cancer" *Clin Sci (Loud).* 2006 March; 110(3):279-91. doi: 10.1042/CS20050175.

Infante et al. "RANKL/RANK/OPG system beyond bone remodeling: involvement in breast cancer and clinical perspectives" *Journal of Experimental & Clinical Cancer Research* (2019) 38:12. https://doi.org/10.1186/s13046-018-1001-2.

Lamoureux et al. "Therapeutic Relevance of Osteoprotegerin Gene Therapy in Osteosarcoma: Blockade of the Vicious Cycle between Tumor Cell Proliferation and Bone Resorption" *Cancer Res* 1 2007 67(15):7308-7318; DOI: 10.1158/0008-5472.CAN-06-4130. T. Martin "Historically significant events in the discovery of RANK/RANKL/OPG" *World J Orthop.* 2013 Oct. 18; 4(4): 186-197. doi: 10.5312/wjo.v4.i4.186.

Liang et al. "Therapeutic effect of low-intensity pulsed ultrasound on temporomandibular joint injury induced by chronic sleep deprivation in rats" *Am J Transl Res.* 2019; 11(6): 3328-3340.

T. Martin "Historically significant events in the discovery of RANK/RANKL/OPG" *World J Orthop.* 2013 Oct. 18; 4(4): 186-197. doi: 10.5312/wjo.v4.i4.186

E. McGrath "OPG/RANKL/RANK Pathway as a Therapeutic Target in Cancer" *Journal of Thoracic Oncology*, September 2011 6(9): 1468-1473; https://doi.org/10.1097/JTO.0b013e318229421f.

D. Novack "Inflammatory osteoclasts, a different breed of bone eaters?" *Arthritis Rheumatol.* 2016 December; 68(12): 2834-2836. doi: 10.1002/art.39835.

Oyajobi, B. "Multiple myeloma/hypercalcemia" *Arthritis Research & Therapy* volume 9, Article number: S4 (2007).

Oranger et al. "Cellular Mechanisms of Multiple Myeloma Bone Disease" *Clinical and Developmental Immunology* Volume 2013, Article ID 289458, 11 pages http://dx.doi.org/10.1155/2013/289458.

Rachner et al. "Prognostic Value of RANKL/OPG Serum Levels and Disseminated Tumor Cells in Nonmetastatic Breast Cancer" *Clin Cancer Res Feb.* 15 2019 (25) (4) 1369-1378; DOI: 10.1158/1078-0432.CCR-18-2482.

Raje et al. "Role of the RANK/RANKL Pathway in Multiple Myeloma" *Clin Cancer Res* 2019 25(1):12-20; DOI: 10.1158/1078-0432.CCR-18-1537.

Sisay et al. "The RANK/RANKL/OPG system in tumorigenesis and metastasis of cancer stem cell: potential targets for anticancer therapy" *Onco Targets Ther.* 2017; 10: 3801-3810.

Van Dam et al. "RANK/RANKL signaling inhibition may improve the effectiveness of checkpoint blockade in cancer treatment" *Critical Reviews in Oncology/Hematology* Volume 133, January 2019, Pages 85-91.

Zdzisińska B, et al. "RANK/RANKL i OPG w szpiczaku plazmocytowym [The role of RANK/RANKL and OPG in multiple myeloma]" *Postepy Hig Med Dosw* (Online). 2006; 60:471-482.

What is claimed is:

1. A bioelectric stimulator programmed to produce at least one bioelectric signal that stimulate(s) target tissue of a subject to increase expression of osteoprotegerin (OPG), thus inhibiting bone degradation in the subject, wherein the bioelectric signal(s) comprise(s):
   (a) a signal of, within 15%, 4.0 milliVolt, 2,000 Hz, square wave; and/or
   (b) a signal of from 3 milliVolt to 5 milliVolt at a frequency range of 1 to 3 MHz, and a duration range of 30 to 40 mW/cm$^2$ for a minimum of 20 minutes,
   wherein the bioelectric stimulator is further programmed to produce further bioelectric signal(s) that increase(s) expression of receptor activator of nuclear factor kappa-B ligand (RANKL) by the tissue, wherein the further bioelectric signal(s) comprise(s):
   (c) 3.0 mV, 2 Hz, square wave,
   (d) 3 mV at 2/100 Hz alternating frequency with current of 3 mA followed by 15 Hz, 1 Gauss EM field, consisting of 5-millisecond bursts with 5-microsecond pulses followed by 200-µs pulse duration at 30 Hz and with current amplitude of 140 mA, and/or
   (e) a biphasic pulse at 20 Hz, 0.1 V, and a 7.8 ms pulse duration.

2. A method of using the bioelectric stimulator of claim 1, to treat a subject, the method comprising:
delivering the bioelectric signals to tissue of the subject to regulate expression of OPG and RANKL by the tissue, wherein the subject has been diagnosed with a disorder selected from the group consisting of cancer, breast cancer, bone cancer, lung cancer, osteoporosis, and a combination of any thereof.

3. The method according to claim 2, wherein the subject has been diagnosed with multiple myeloma.

4. The method according to claim 2, further comprising:
separately delivering to the subject an admixture comprising any combination of the following: stem cells, endothelial progenitor cells, selected exosomes, selected alkaloids, selected anti-inflammatory agents, nutrient hydrogel, organ-specific matrix, selected growth factors, amniotic fluid, placenta fluid, cord blood, and embryonic sourced growth factors and cells.

5. A bioelectric stimulator programmed to produce at least one bioelectric signal that stimulates target tissue of a subject to increase expression of osteoprotegerin (OPG), thus inhibiting bone degradation in the subject, wherein the bioelectric signal comprises:
(a) a signal of, within 15%, 4.0 milliVolt, 2,000 Hz, square wave,
wherein the bioelectric stimulator is further programmed to produce further bioelectric signal(s) that increase(s) expression of receptor activator of nuclear factor kappa-B ligand (RANKL) by the tissue, wherein the further bioelectric signal(s) comprise(s):
(b) 3.0 mV, 2 Hz, square wave,
(c) 3 mV at 2/100 Hz alternating frequency with current of 3 mA followed by 15 Hz, 1 Gauss EM field, consisting of 5-millisecond bursts with 5-microsecond pulses followed by 200-μs pulse duration at 30 Hz and with current amplitude of 140 mA, and/or
(d) a biphasic pulse at 20 Hz, 0.1 V, and a 7.8 ms pulse duration.

6. A method of using the bioelectric stimulator of claim 5, to treat a subject, the method comprising:
delivering the bioelectric signals to tissue of the subject to regulate expression of OPG and RANKL by the tissue, wherein the subject has been diagnosed with a disorder selected from the group consisting of cancer, breast cancer, bone cancer, lung cancer, osteoporosis, and a combination of any thereof.

7. The method according to claim 6, wherein the subject has been diagnosed with multiple myeloma.

8. A bioelectric stimulator programmed to produce at least one bioelectric signal that stimulate(s) target tissue of a subject to increase expression of osteoprotegerin (OPG), thus inhibiting bone degradation in the subject, wherein the bioelectric signal(s) comprise(s):
(a) a signal of from 3 milliVolt to 5 milliVolt at a frequency range of 1 to 3 MHz, and a duration range of 30 to 40 mW/cm$^2$ for a minimum of 20 minutes, wherein the bioelectric stimulator is further programmed to produce further bioelectric signal(s) that increase(s) expression of receptor activator of nuclear factor kappa-B ligand (RANKL) by the tissue, wherein the further bioelectric signal(s) comprise(s):
(b) 3.0 mV, 2 Hz, square wave,
(c) 3 mV at 2/100 Hz alternating frequency with current of 3 mA followed by 15 Hz, 1 Gauss EM field, consisting of 5-millisecond bursts with 5-microsecond pulses followed by 200-μs pulse duration at 30 Hz and with current amplitude of 140 mA, and/or
(d) a biphasic pulse at 20 Hz, 0.1 V, and a 7.8 ms pulse duration.

9. A method of using a bioelectric stimulator programmed to produce at least one bioelectric signal that stimulates target tissue in a subject to increase expression of osteoprotegerin (OPG), wherein the at least one bioelectric signal comprises:
a signal of from 3 milliVolt to 5 milliVolt at a frequency range of 1 to 3 MHz, and a duration range of 30 to 40 mW/cm$^2$;
to treat a subject, the method comprising:
delivering the at least one bioelectric signal to tissue of the subject for a minimum of 20 minutes so as to increase expression of OPG by the tissue, thus inhibiting bone degradation in the subject,
wherein the subject has been diagnosed with a disorder selected from the group consisting of cancer, breast cancer, bone cancer, lung cancer, osteoporosis, and a combination of any thereof.

10. The method according to claim 9, wherein the subject has been diagnosed with multiple myeloma.

11. The method according to claim 9, further comprising:
delivering further bioelectric signal(s) to increase the expression of receptor activator of nuclear factor kappa-B ligand (RANKL) to tissue of the subject,
wherein the further bioelectric signals to increase the expression of RANKL by the tissue are selected from the group consisting of
3.0 mV, 2 Hz, square wave;
3 mV at 2/100 Hz alternating frequency with current of 3 mA followed by 15 Hz, 1 Gauss EM field, consisting of 5-millisecond bursts with 5-microsecond pulses followed by 200-μs pulse duration at 30 Hz and with current amplitude of 140 mA;
a biphasic pulse at 20 Hz, 0.1 V, and a 7.8 ms pulse duration; and
a combination of any thereof.

12. The method according to claim 11, wherein the subject has been diagnosed with multiple myeloma.

\* \* \* \* \*